(12) United States Patent
Shen et al.

(10) Patent No.: US 8,389,484 B2
(45) Date of Patent: Mar. 5, 2013

(54) METHODS FOR TARGETING RNA MOLECULES

(76) Inventors: Ling X. Shen, Marlboro, MA (US); Gregory L. Verdine, Lexington, MA (US); James P. Basilion, Brookline, MA (US); Vincent P. Stanton, Jr., Belmont, MA (US)

(*) Notice: Subject to any disclaimer, the term of this patent is extended or adjusted under 35 U.S.C. 154(b) by 178 days.

(21) Appl. No.: 10/999,171

(22) Filed: Nov. 29, 2004

(65) Prior Publication Data

US 2005/0137158 A1 Jun. 23, 2005

Related U.S. Application Data

(62) Division of application No. 10/256,987, filed on Sep. 26, 2002, now Pat. No. 7,115,372, which is a division of application No. 09/515,721, filed on Feb. 29, 2000, now Pat. No. 6,686,148.

(60) Provisional application No. 60/122,199, filed on Mar. 1, 1999.

(51) Int. Cl.
*C12N 15/11* (2006.01)
*C12N 15/113* (2010.01)
*C12N 15/115* (2010.01)
*C12Q 1/68* (2006.01)

(52) U.S. Cl. ............... 514/44 A; 514/1; 514/2; 435/455; 435/6.1; 435/7.8

(58) Field of Classification Search ................... None
See application file for complete search history.

(56) References Cited

U.S. PATENT DOCUMENTS

| | | | | |
|---|---|---|---|---|
| 5,108,921 | A | * 4/1992 | Low et al. | 435/375 |
| 5,391,723 | A | * 2/1995 | Priest | 536/23.1 |
| 5,583,032 | A | * 12/1996 | Torrence et al. | 435/91.1 |
| 5,702,890 | A | 12/1997 | Housman | 435/6 |
| 6,200,754 | B1 | * 3/2001 | Housman et al. | 435/6 |
| 6,214,545 | B1 | 4/2001 | Dong et al. | 435/6 |
| 7,115,372 | B2 | * 10/2006 | Shen et al. | 435/6.13 |

FOREIGN PATENT DOCUMENTS

WO WO97/33897 9/1997

OTHER PUBLICATIONS

Detering et al., "Validation of Automated Docking Programs for Docking and Database.." J. Med. Chem. 47:4188-4201, 2004.
Hermann, T., "Strategies for the Design of Drugs Targeting RNA and RNA-Protein Complexes" Angew. Chem. Int. Ed., 39:1890-1905, 2000.
Hwang et al., "Inhibition of Gene Expression in Human Cells Through Small . . . " PNAS 96:12997-13002, 1999.
Millington-Ward et al., "Strategens in vitro for Gene Therapies Directed to Dominant Mutations" Human Mol. Genet. 6:1415-1426, 1997.
Shen et al., "Single0nucleotide Polymorphisms Can Cause Different Structural.." PNAS 96:7871-7876, 1999.
Wilson et al., "Targeting RNA with Small Molecules" Curr. Med. Chem. 7:73-98, 2000.
Amara et al., "A versatile synthetic dimerizer for the regulation of protein-protein interactions" Proc. Natl. Acad. Sci USA 94:10618-10623, 1997.
Crabtree et al., "There-part inventions: intracellular signaling and induced proximity" Trends in Biochem. Sci. 21(11-1):418-422, 1996.
Mei et al., "Inhibitors of Protein-RNA Complexation that Target the RNA: . . . " Biochemistry 37:14204-14212, 1998.
Werstuck et al., "Controlling Gene Expression in Living Cells Through Small Molecule-RNA Interactions" Science 282:296-298, 1998.

* cited by examiner

*Primary Examiner* — Maria Marvich
(74) *Attorney, Agent, or Firm* — Fish & Richardson P.C.

(57) ABSTRACT

Described are methods for identifying targets in RNA molecules based on differences in RNA secondary structure related to sequence variances between different allelic forms. Also described are methods for identifying or developing small molecules which can be used to modulate a target RNA by creation of protein-small-molecule-RNA complexes, as well as compositions which include such small molecules and methods of using those small molecules and compositions.

12 Claims, 9 Drawing Sheets

AARS-1013U/C mRNA

U-allele

```
         A  U 1013 (SNP)
        C      G
        C      C
         A • U
         G • C
         U • G
         C • G
         G • C  A
    999  G • C
5'---G G G U G C U • A --- 3'
```

C-allele

```
              U  G
             C    A
             G • C
             G • C
            C U • A
             G • C 1013 (SNP)
             U • G
         999 G • C
             G • U
             G • C
             C • G
       5'--- C • G --- 3'
```

FIG. 2A

RPA70-1674U/C mRNA

U-allele

C-allele

1  5' (1684)TAGCTTCAGCAGACTCCTGG(1665) 3'
2  5' (1682)GCTTCAGCGGACTCCTGG(1665) 3'
3  5' (1661)CAAGTCACCCACTGATTCTC(1642) 3'
4  5' GAATCAAGTCACCCACTGATTCTC 3'
5  5' GAGAATCAAGTCACCCACTGATTCTC 3'
6  5' (1661)CAAGTCACCCACTGA(1647) 3'

| % Cleavage | +1 | +2 | +3 | +4 | +5 | +6 |
|---|---|---|---|---|---|---|
| U-allele | 2.1 | 0.2 | 53.6 | 41.0 | 34.5 | 28.4 |
| C-allele | 0.1 | 2.0 | 4.8 | 3.7 | 3.0 | 1.6 |

(1) Hydrocarbon chains of various lengths and chemical composition. For example:

(2) Linkers built from planer aromatic hydrocarbon ring systems. Points of attachment (illustrated by •) may be any two different Carbon atoms.
For example:

(3) Linkers built from carbohydrates (saccharides).
Points of attachment (illustrated by •) may be anywhere on each sugar ring.
For example:

(4) Linkers using β-lactam containing ring systems such as cephans as building blocks.
For example:

METHODS FOR TARGETING RNA MOLECULES

RELATED APPLICATION

This application is a divisional and claims the benefit of priority under 35 USC 120 of U.S. application Ser. No. 10/256,987, filed Sep. 26, 2002, now U.S. Pat. No. 7,115,372, which is a divisional of U.S. application Ser. No. 09/515,721, filed on Feb. 29, 2000, now U.S. Pat. No. 6,686,148, which claims priority from U.S. Provisional Application Ser. No. 60/122,199, filed on Mar. 1, 1999. The disclosures of the prior applications are considered part of and are incorporated by reference in the disclosure of this application.

BACKGROUND

This application relates to the field of identification of compounds active on RNA and of target sites on the RNA.

The wealth of information gained from the study of the human genome has allowed identification of many genes whose inappropriate expression results in disease. To exploit this information, several technologies have been developed to specifically target gene expression. Modulating the expression of such genes allows treatment of the disease. In particular, the strategy of modulating gene expression by targeting RNA has spawned several new classes of rationally designed therapeutics (e.g., ribozymes, DNAzymes, and antisense oligonucleotides). However, to date, these technologies have had very limited clinical success. One of the reasons for the limited success is due to the difficult pharmacological barriers these macromolecules must overcome.

The pharmacological treatment of disease is one of the signal advances in medicine in the twentieth century. Modern methods of small molecule development have also proven highly useful in allied fields such as veterinary medicine and pest eradication in agriculture. An ever increasing number of diseases can be ameliorated by appropriate drug therapy, reflecting increasing knowledge of disease pathophysiology and improved methods for conducting clinical research. As the sequence of the human (and other) genomes is solved and the molecular understanding of disease advances it will increasingly be possible to select optimal targets for therapeutic attack. Thus while many current drug treatments act by poorly understood mechanisms, and/or provide only symptomatic relief, increasingly it should be possible to reverse disease pathophysiology and provide more specific and potent therapeutic relief. To achieve this goal, however, will require improved methods of drug development. In particular, the development of drug targeting strategies that enable highly specific targeting of selected genes or gene products will be of great use.

The information provided and references cited herein are provided solely to assist the understanding of the reader, and is not admitted to be prior art to the present invention.

SUMMARY OF THE INVENTION

The present invention provides certain advantageous methods for developing biologically active molecules. The invention includes a new method for targeting RNA with small molecules, where the small molecule makes contact with both a cellular protein and a cellular RNA. The effect of the tripartite complex is to increase the affinity of the complex beyond what could be achieved alone with the small molecule and the RNA. This addresses what is believed to be the major limitation of current attempts to target RNA with small molecules, the lack of specific high affinity binding of small molecules to RNAs, which are much more flexible than proteins. This is a generic method for inhibiting any cellular RNA, as described in the disclosure, including, but not limited to allele specific inhibition or inhibition based on targeting to identified regions of RNA secondary structure where that secondary structure differs between allelic forms.

The invention also provides a method for identifying RNA targets for allele specific therapy. These methods have application in at least two major areas: (1) autosomal dominant diseases, or diseases of excess gene dosage, where elimination of one mRNA (but not both) would have a therapeutic effect and (2) cancer and other diseases with LOH where allele specific therapy will provide a differential effect on disease tissue compared to normal tissue. Such use of allele specific therapy has been described in Housman, U.S. Pat. No. 5,702,890, issued Dec. 30, 1997 and Housman et al., U.S. patent application Ser. No. 09/045,053, filed Mar. 19, 1998 which are hereby incorporated by reference in their entireties including drawings. Targeting of different alleles can, for example, involve the use of protein-small molecule complexes as described below, but is not limited to such complexes. For example, different alleles can be targeted with small molecules or with oligonucleotide inhibitors.

The present invention provides a unique strategy for targeting cellular RNAs. This new method overcomes the limitations of current approaches with respect to affinity and specificity. The invention entails formation of a trimolecular complex involving the target RNA, a small molecule, and a cellular protein. The recruitment of a specific cellular protein to the RNA:small molecule complex has the advantage of substantially increasing the area of binding due to contacts between the protein and the RNA, and thereby increase the affinity of the complex beyond what could be achieved alone with the small molecule and the RNA by cooperative binding generally involving electrostatic, hydrogen bonding, and hydrophobic interactions. These favorable binding interactions will increase the affinity of the complex beyond what could be achieved with a small molecule and RNA.

The present invention also provides a new class of RNA therapeutic targets that will provide the basis for inhibition, e.g., allele specific inhibition, by small molecules, and methods for identifying such targets in candidate RNAs. The basis of the invention is the novel observation that single nucleotide polymorphisms in mRNAs are associated with altered secondary structures. These structural differences, not previously known to be associated with normal allelic variation, provide scope for allele specific small molecule inhibition of RNA. Also described are methods for producing and identifying small molecule inhibitors of RNAs.

Thus, in a first aspect the invention provides a method for identifying a potential small molecule inhibitor, where the inhibition involves the induction of formation of a complex of a cellular RNA, a small molecule inhibitor, and a cellular protein. The potential small molecule inhibitor includes a first and a second moiety joined by a linker. The method involves identifying a first moiety which binds to at least a portion of a selected cellular protein; and also identifying a second moiety which binds to at least a fragment of a cellular RNA. Such joint binding indicates that the small molecule is a said potential small molecule inhibitor. The inhibitory ability of the small molecule can be tested by standard methods, e.g., testing the level of protein synthesis from a target mRNA. Clearly, the identifications of the moieties can be performed in either order. The method can also involve selection of a linker or provision of a standard linker, e.g., based on prior screening. In certain cases the linker need not be separate from the first or second moiety, but may be a part of one or both moieties.

In this context, the term "potential small molecule inhibitor" refers to a small molecule which binds to both a selected protein and a target RNA but for which the ability to inhibit a biological activity (e.g., reduce the rate or amount of protein translation from an mRNA) of the RNA has not yet been tested. Following confirmation of such inhibitory characteristic, the small molecule can be referred to as a "small molecule inhibitor" or "inhibitor".

The term "small molecule" refers to a compound which has a molecular mass equal to or less than 5000 Daltons (5 kD), preferably less than 3 kD, still more preferably less than 2 kD, and most preferably less than 1 kD. In some cases it is highly preferred that a small molecule have a molecular, mass equal to or less than 700 Da.

The term "inhibitor" refers to a compound that reduces to a statistically significant extent at least one activity of a reference compound. In the context of this invention, an inhibitor generally reduces an activity of an RNA, most commonly, but not limited to, reducing or eliminating the rate and/or extent of translation of an mRNA, reducing or eliminating processing of a pre-mRNA to produce a mature RNA; reducing or eliminating transport of an mRNA from nucleus to cytoplasm, or reducing or eliminating a regulatory function of an RNA molecule. Preferably the reduction in activity is sufficient to detect based on gross observation of cellular properties, e.g., growth rate, survival, morphology, and is preferably sufficient and of a nature to produce a therapeutic response in a patient in whom reduction in the expression of the target gene would be beneficial.

In the context of this invention, the phrase "induction of formation of a complex" refers to a property of a small molecule which results in a structure which includes multiple molecules, especially a protein-small molecule-RNA complex, where the components other than the small molecule would not associate with each other or not associate with each other in the same physical relationship to any appreciable extent in the absence of the small molecule or other component which induces formation of the complex. In some cases other molecules may be present in the complex.

In the context of this invention, the term "trimolecular complex" refers to an association or complex which includes a selected protein, a small molecule, and a target RNA. Other components may also be present, e.g., additional proteins or polypeptides, small ions, or water. Preferably, however, the selected protein and the target RNA are the only macromolecules present in the complex. Preferably the stably associated complex consists essentially of or consists of the specified types of molecules.

In preferred embodiments, the identifying of the first moiety involves identifying a known small molecule ligand of the cellular protein. By utilizing a known small molecule ligand (including analogs which retain binding to the protein), it is not necessary to search for a binding moiety, but only to confirm that binding occurs to the selected protein when the ligand is attached to the linker and the second moiety.

In preferred embodiments, the method involves providing a small molecule library containing compounds comprising or consisting essentially of the first moiety and the linker attached to variable second moieties, and screening the library to identify one or more molecules such that the second moiety binds to the target RNA. Preferably the identifying a second moiety involves providing a small molecule library in which compounds have a first moiety which binds to said selected cellular protein, a linker, and a variable second moiety; and screening compounds of the library to identify a compound which binds to the target RNA or fragment thereof. The fragment includes sufficient sequence to retain the characteristics utilized for binding of such molecules to the intact RNA, e.g., local secondary structure.

In reference to selected proteins and target RNA for binding of a first moiety and a second moiety respectively, the terms "fragment" and "portion" refer to a part of the sequence of the intact protein or RNA which retains properties of the molecule important for selecting binding. Preferably the fragment or portion retains the local secondary structure as in the intact molecule. For proteins, a portion is preferably at least 10 amino acid residues in length, more preferably at least 20, and still more preferably at least 40 amino acid residues. RNA fragments are preferably at least 20 nucleotides in length, more preferably at least 50 nucleotides in length, and still more preferably at least 100 nucleotides in length.

Reference to "variable" moieties or linkers in a plurality of compounds or molecules or in a library of such compounds means that different molecules in the group have different moieties or linkers as specified.

Conversely, the term "fixed" in connection with a moiety or linker in a plurality of compounds (including in a library, e.g., a combinatorial library) means that compounds in the plurality have the same specified moiety or linker.

In preferred embodiments the method involves identifying the first moiety by providing a small molecule library of compounds which have a variable first moiety, a linker, and a fixed second moiety, and screening compounds of the library to identify a compound which binds to the selected cellular protein or portion thereof.

In cases where a known ligand for a selected protein is used, preferably the protein and its ligand are selected from adenosine triphosphate analogs, which could sequester one or more cellular ATPases; flavin adenine dinucleotide or FAD analogs; nicotinamide or nicotinamide analogs; folates or folate analogs, which could sequester proteins such as dihydrofolate reductase, thymidylate synthase or other abundant proteins which require folate as a cofactor; cyclosporin, FK506, rapamycin, and coumermycin or their synthetic analogs, which bind to FK506 Binding Protein (FKBP).

In preferred embodiments, the process of identifying the first or second moieties or the linker involves two or more iterations of at least one of the identification steps. This can be performed to improve the characteristics of the small molecule, e.g., the binding affinity for either or both of the selected protein or target RNA or to improve overall complex stability.

In preferred embodiments, the protein constituent of the trimolecular complex is a cellular protein that is present in the cellular compartment(s) in which the target RNA is present.

Preferably the protein constituent of the trimolecular complex is a protein with known RNA binding activity. Such selection can be advantageous as it is already known that the protein has properties which allow stable interaction with RNA, an interaction which can be utilized in the formation of the desired complex.

Preferably the protein constituent of the trimolecular complex is an RNase, for example an RNase from one of the classes RNaseH type 1, RNaseH type 2, and RNaseL; or an RNA helicase.

In preferred embodiments the protein constituent of the trimolecular complex is an DNA binding protein. Such molecules also provide advantageous nucleic acid binding properties.

In preferred embodiments, the protein constituent of the trimolecular complex has a two or more basic residues within 10 Angstroms of the small molecule binding site thereby providing favorable charge interactions with the target RNA.

As indicated, the molecules are small molecules, which preferably do not exceed 4000 Daltons in molecular mass, more preferably do not exceed 3000 Daltons, still more preferably do not exceed 2000 Daltons, and still more preferably do not exceed 1000 Daltons, or even 700 Daltons.

In preferred embodiments, the targeted cellular RNA is a pre-mRNA or an mRNA. The term "mRNA" is used in its usual sense as understood by those skilled in the art. The term "pre-mRNA" refers to an RNA transcript which will undergo processing to become an mRNA. Commonly the pre-mRNA contains additional RNA sequence which will be removed to form the mature mRNA.

In preferred embodiments the targeted cellular RNA has at least one polymorphism that results in an altered secondary structure and the altered secondary structure is the target of the RNA binding moiety of said small molecule.

In connection with an RNA, a "sequence polymorphism" or "polymorphism" is a difference in nucleotide sequence between RNAs transcribed from different allelic forms of a particular gene. Most often, a polymorphism is a single nucleotide substitution. A polymorphism, either alone or in conjunction with one or more other polymorphisms can result in a change in RNA secondary structure, e.g., as shown by changes in digestion with various RNases.

Preferably the targeted cellular RNA is an RNA bearing a mutation that alters secondary structure of the RNA, or that exists on the same allele as another site of variation that alters the secondary structure of the RNA.

The term "allele" refers to one specific form of a gene within a cell or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". The term "alternative allele", "alternative form", or "allelic form" refers to an allele that can be distinguished from other alleles by having distinct variances at at least one, and frequently more than one, variant site within the gene sequence.

In preferred embodiments, the method further involves providing a plurality of small molecules which contain a plurality of different linkers and a first moiety identified as described above, or a second moiety identified as described above or both; and screening the plurality of small molecules to identify a potential small molecule inhibitor with advantageous binding or pharmacologic characteristics. The further step of varying the linker can allow selection of a linker which allows more beneficial presentation or association of the protein and the RNA.

In preferred embodiments, the identification of the second moiety involves providing a small molecule library containing compounds containing fixed first moiety and linker attached to variable second moieties; and screening the library to identify one or more molecules in which the second moiety binds to the target RNA. Preferably the identification of the first moiety involves providing a small molecule library of compounds which contain a variable first moiety, a linker, and a fixed second moiety identified as just described; and screening compounds of the library to identify a compound which binds to the selected cellular protein or portion thereof.

In a second aspect, the invention provides a method for identifying an RNA target for an allele specific therapeutic small molecule, e.g., an inhibitor, by identifying at least one sequence variance in the RNA target in a population of interest, determining whether the RNA secondary structure of any sequence variants identified differs between variant alleles. A difference in the RNA secondary structure is indicative that the sequence variance is a potential target for an allele specific therapeutic small molecule.

An "allele specific inhibitor" or "variance specific inhibitor" is a drug or inhibitor that inhibits the activity of one alternative allele of a gene to a greater degree than at least one other alternative allele. The difference in activity is commonly determined by the dose or level of a drug required to achieve a quantitative degree of inhibition. A commonly used measure of activity is the IC50 or concentration of the drug required to achieve a 50% reduction in the measured activity of the target gene.

Preferably an allele specific inhibitor will have at least twice the activity on the target allelic form than on a non-target allelic form, more preferably at least 5 times, still more preferably at least 10 times, and still more preferably at least 50 times, and most preferably at least 100 times. This can also be expressed as the sensitivities of the different allelic forms to the inhibitor. Thus, for example, it is equivalent to state that the target allelic form is most preferably at least 100 times as sensitive to the inhibitor as a non-target allelic form. The activity of an inhibitor can be measured either in vitro or in vivo, in assay systems that reconstitute the in vivo system, or in systems incorporating selected elements of the complete biological system. For use in inhibiting cells containing only the target allelic form rather than cells containing at least one non-targeted allelic form, the difference in activity is preferably sufficient to reduce the proliferation rate or survival rate of the cells having only the targeted allelic form to no more than one half of the proliferation rate or survival rate of cells having at least one non-targeted allelic form. More preferably, the fraction is no more than $\frac{1}{5}$ or $\frac{1}{10}$, and still more preferably no more than $\frac{1}{20}$, $\frac{1}{50}$, $\frac{1}{100}$, or even lower.

In this context, the term "population" refers to a group of individuals (generally a group of humans) distinguishable from other groups. Bases for distinguishing can, for example, include geography, familial relationship, racial background, age, gender, and combinations of these factors. A "population of interest" is thus a group of individuals which are relevant to identification of a target, a therapeutic or complex-forming agent, or a method of using or making such agents or other aspect of this invention, e.g., a group to which a patient belongs in most cases a population will preferably encompass at least ten thousand, one hundred thousand, one million, ten million, or more individuals, with the larger numbers being more preferable. In special circumstances, diseases will occur with high frequency in specific geographical regions or within specific familial, racial, or cultural groups, and a relevant population may usefully be considered to be a smaller group.

Preferably, the sequence variance to be targeted occurs in an allele frequency range between 0.1:0.9 and 0.5:0.5 in a population of interest.

The term "allele frequency" refers to the fraction (or frequency of occurrence) of a specific allele as compared to all alleles in a population. It is recognized in the art that the heterozygote frequency and allele frequency are related and, for certain alleles, can be described by Hardy Weinberg equilibrium calculations. It will also be recognized that sequence variances that occur at high frequency in the population are commonly not deleterious to the health of the individuals who carry these genes and are commonly not disease genes or mutations that are associated with disease.

In preferred embodiments, the determination of the RNA secondary structure is performed using one or more structure-specific enzymes, e.g., a nuclease, preferably selected from T1, T2, S1, U2, CL3, V1, A, PhyM, N.c. nuclease or RNase; or by chemical probing with a chemical selected from the group consisting of dimethyl sulfate, diethylpyrocarbonate, CMCT, kethoxal, bisulfite, ethylnitrosourea, MPE-Fe(II), and Fe(II)-EDTA.

Allele specific targeting can advantageously be applied in abase where the target RNA is an allele that, if reduced in abundance, would at least ameliorate a disease state. The amelioration can, for example, be symptomatic relief, reduction or elimination of one or more deleterious effects of the disease, or even cure of the disease.

Likewise, the target RNA can be an allele associated with an autosomal dominant disease, such as Huntington's disease, or other diseases shown in Table 1.

The target RNA can also be an allele of an essential gene which undergoes loss of heterozyosity in a proliferative disorder, e.g., a cancer. For example, the targets identified by the methods herein can advantageously be utilized in the therapeutic approach described in Housman, supra.

The term "proliferative disorder" refers to various cancers and disorders characterized by abnormal growth of somatic cells leading to an abnormal mass of tissue which exhibits abnormal proliferation, and consequently, the growth of which exceeds and is uncoordinated with that of the normal tissues. The abnormal mass of cells is referred to as a "tumor", where the term tumor can include both localized cell masses and dispersed cells, The term "cancer" refers to a neoplastic growth and is synonymous with the terms "malignancy", or "malignant tumor". The treatment of cancers and the identification of anticancer agents is the concern of certain preferred embodiments of the aspects of the present invention. Other abnormal proliferative diseases include "nonmalignant tumors", and "dysplastic" conditions including, but not limited to, leiomyomas, endometriosis, benign prostate hypertrophy, atherosclerotic plagues, and dysplastic epithelium of lung, breast, cervix, or other tissues. Drugs used in treating cancer and other non-cancer proliferative disorders commonly aim to inhibit the proliferation of cells and are commonly referred to as antiproliferative agents.

In preferred embodiments, the allele specific small molecule is a small molecule inhibitor containing a first moiety which binds to a selected cellular protein or a portion thereof; a second moiety which binds to a target cellular RNA or a fragment thereof, and a linker connecting the first moiety and the second moiety, where the small molecule inhibitor can bind to the selected cellular protein and to the target cellular RNA to form a complex. The molecule can be as further described for those identified in the first aspect above and for corresponding pharmaceutical compositions and complex-forming molecules.

In a third aspect, the invention provides a method for identifying an allele specific RNA binding small molecule for a target RNA, involving the steps of identifying at least one sequence variance in the RNA target in a population of interest having secondary structure differences between variant alleles, screening the two RNA structures for a said sequence variance or variances for binding to or inhibition by a plurality of small molecules; and identifying a compound that preferentially binds to or inhibits one of said RNA structures, where the binding or inhibition is indicative that the compound is an allele specific RNA binding small molecule. Preferably the plurality of small molecules are elements of a small molecule combinatorial library.

Preferably the method includes determining whether the allele specific RNA binding small molecule provides a cellular activity, by contacting cells producing the target RNA with the allele specific RNA binding small molecule; and determining whether the small molecule produces a change in cellular activity. Thus, the method uses a cellular assay to identify cellular effects. Preferably the cellular effect or activity is a decrease in expression of the target RNA or the translation product.

As in preceding aspects, the target RNA is preferably a pre-mRNA or an mRNA.

In preferred embodiments, the plurality of small molecules is a plurality of potential small molecule inhibitors each comprising a first moiety which may be the same or different and a second moiety which differs between the plurality of small molecules and a linker joining the first moiety and the second moiety. The first moiety is selected to bind to a selected cellular protein or a portion thereof; and the second moiety is selected to bind to a target cellular RNA or a fragment thereof, thereby forming a trimolecular complex.

Additional preferred embodiments are as described for the first aspect above.

In a fourth aspect, the invention provides a pharmaceutical composition which includes a small molecule inhibitor where the inhibitor includes a first moiety which binds to a selected cellular protein or a portion thereof; a second moiety which binds to a target cellular RNA or a fragment thereof, and a linker connecting said the moiety and the second moiety, where the small molecule inhibitor can bind to the selected cellular protein and to the target cellular RNA to form a complex. The composition also includes a pharmaceutically acceptable carrier, excipient, or diluent. Generally the inhibitor will be a synthetic molecule.

In the context of the inhibitor or binding compounds of this invention, the term "synthetic" indicates that the compound has been prepared in whole or in part by the intervention of humans, and is not a compound naturally produced by a naturally occurring organism. A portion or even most of a synthetic molecule can be produced by an organism, and then modified by synthetic methods. Alternatively, most or all of a molecule can be prepared by synthetic methods, and the resulting molecule is then referred to as "fully synthetic".

In certain cases, a naturally occurring molecule may be found which has the complex-forming properties described. Such a molecule could be used in the methods described herein for using compounds which inhibit or bind RNA, or could be modified to alter its binding and/or activity characteristics.

Preferably the selected protein is a human protein; preferably the target RNA is a human RNA.

Preferably the small molecule inhibitor inhibits expression of said target RNA.

In preferred embodiments the small molecule inhibitor has differential activity on variant forms of the RNA differing in secondary structure, where the difference in secondary structure is related to at least one sequence variance. Preferably the targeted cellular RNA has a polymorphism that results in an altered secondary structure and the altered secondary structure is the target of the RNA binding moiety of said small molecule.

Also in preferred embodiments, the inhibitor is a compound as identified in the first aspect above and/or the target is as identified in the second aspect.

In a fifth aspect, the invention provides a method for inhibiting expression of an mRNA. The method involves contacting cells normally expressing the mRNA with a small molecule inhibitor. The inhibitor has a first moiety which binds to a selected cellular protein or a portion thereof; a second moiety which binds to a target cellular mRNA, and a linker connecting the first moiety and the second moiety. The small molecule inhibitor can bind to the selected cellular protein and to the target cellular mRNA to form a complex.

In preferred embodiments the molecule and/or target is as described for embodiments of aspects above.

In a sixth aspect, the invention provides a method for treating an autosomal dominant or gene dosage disease, by administering to a patient suffering from such a disease a therapeutically effective amount of an allele specific RNA inhibitor preferentially active on an allelic form of a target RNA in which at least one sequence variance provides a difference in secondary structure and wherein the allele specificity involves that difference in secondary structure.

In preferred embodiments, the disease is an autosomal dominant disease, and the patient is heterozygous for the gene corresponding to the target RNA.

Also in preferred embodiments, the disease is a gene dosage disease, and said administering is adjusted to reduce but not eliminate expression of the gene. Preferably the patient is heterozygous for the gene and the inhibitor preferentially reduces or eliminates expression of only one allele.

The term "gene dosage disease" refers to a disease which is at least partially has a cause based on overactivity of a product of a gene, e.g., overexpression of the gene.

A "therapeutic effect" results, to some extent, in a measurable response in the treated disease or condition. Thus, a therapeutic effect can, for example, include a cure, or a lessening of the growth rate or size of a lesion such as a tumor, or an increase in the survival time of treated patients compared to controls, a relief of a deleterious symptom, or a slowing of the progression of a disease, among other possible effects.

The term "therapeutic amount" means an amount which, when administered appropriately to a patient e.g., a mammal, e.g., a human, suffering from a disease or condition, produces a therapeutic effect.

In preferred embodiments, the molecule and/or target is as described for aspects and embodiments above.

In a seventh aspect, the invention provides a method of treating a patient suffering from a disease or condition, by administering to the patient an allele specific inhibitor of a target RNA where the allele specificity involves a difference in secondary structure related to at least one sequence variance.

In preferred embodiments, the method involves determining the presence of the at least one sequence variance in the patient.

In preferred embodiments, the inhibitor and/or the target is as described for aspects or embodiments above.

In an eighth aspect, the invention provides a method for producing a pharmaceutical agent, by identifying a small molecule inhibitor of a cellular RNA. The inhibitor induces formation of a complex with a cellular protein and the inhibitor includes a first moiety and a second moiety and a linker joining the first moiety and the second moiety. The method involves identifying a first moiety which binds to a selected cellular protein or a portion thereof; and identifying a second moiety which binds to a target cellular RNA or a fragment thereof, and synthesizing the small molecule inhibitor in an amount sufficient to provide a therapeutic response when administered to a patient. The identification can also involve selecting a linker which allows advantageous complex formation.

In preferred embodiments, the inhibitor is preferentially active on an allelic form of an mRNA in which at least one sequence variance provides a difference in RNA secondary structure.

Further preferred embodiments include embodiments as specified in the first and/or second aspects.

In the methods of inhibiting an RNA and/or methods of treating a patient, a compound may be used in various ways, for example, the compound may be used alone, or may be used as part of a pharmaceutical composition.

In a ninth aspect, the invention provides a complex-forming molecule which includes a first moiety which binds to a selected cellular protein or a portion thereof; a second moiety which binds to a target cellular RNA or a fragment thereof, and a linker connecting said first moiety and said second moiety. The small molecule inhibitor can bind to the selected cellular protein and to the target cellular RNA to form a complex.

In preferred embodiments the molecule will inhibit expression of a target mRNA under translation conditions.

"Translation conditions" refers to conditions such that translation would occur from a particular selected mRNA in the absence of an inhibitor of translation. Thus, such conditions can include where an in vitro translation system is, present as well as in vivo conditions.

In preferred embodiments, the selected cellular protein is an RNA binding protein or a derivative thereof.

Further preferred embodiments are as described for the inhibitors in pharmaceutical compositions herein and/or has components, properties, targets or binding pairs as otherwise described herein.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features, advantages and embodiments will be apparent from the following Detailed Description of the Preferred Embodiments and from the Claims.

DETAILED DESCRIPTION OF THE PREFERRED EMBODIMENTS

Figure 1A:
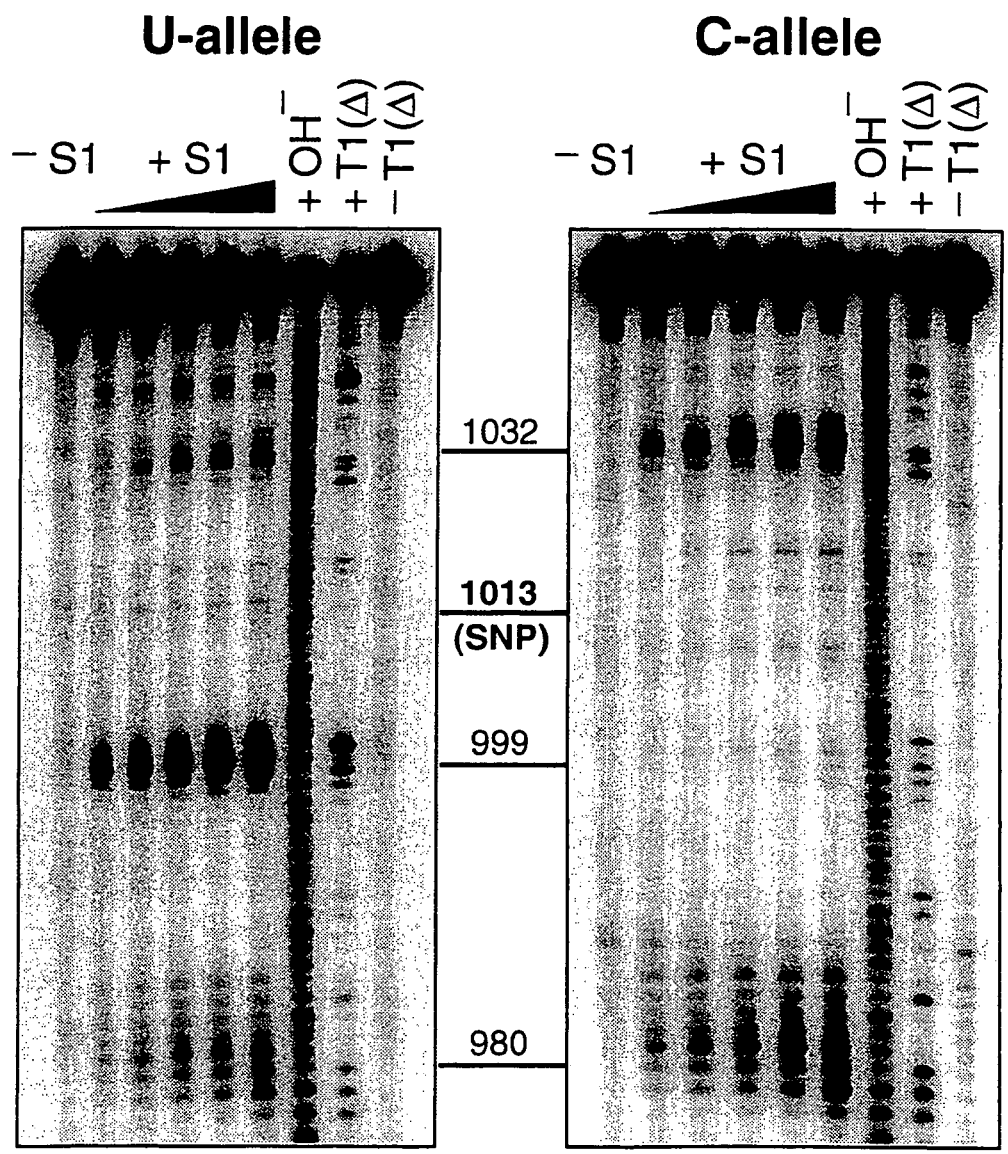
FIG. 1. Nuclease S1 mapping of allelic mRNA structures. −S1, control reaction without S1 added; +S1, Partial digestion by S1 at 37° C. with increasing S1 concentration; +OH⁻, alkaline hydrolysis reaction; +T1(Δ), partial digesion by T1 at 55° C. to create a G-ladder to allow determination of cleavage sites; −T1(Δ), control reaction without T1 added. a, Mapping of accessible single-stranded regions of the U- and C-alleles of a 113-mer fragment (nucleotides 951-1063) of AARS mRNA. b, Mapping of accessible single-stranded regions of the U- and C-alleles of a 544-mer fragment (nucleotides 1378-1921) of RPA70 mRNA. Polymorphic positions are indicated in boldface and labeled SNP.

The development of therapeutic compounds has been and for the foreseeable future will continue to be a costly and time consuming process with only a modest rate of success. The vast majority of current drugs, as well as the majority of drugs in development are small molecules directed to protein targets. Small molecules have a number of attractive pharmaceutical properties compared to other classes of therapeutic compounds, including high potency, oral availability, effective access to most cellular compartments, economical manufacturing and formulation costs and stability. However, some limitations of small molecule drug development are that (1) current technology is best suited to protein targets, despite the fact that in some diseases the most desirable therapeutic end may be total elimination of a particular protein, (2) some protein targets are not amenable to small molecule modulation, often because they lack the hydrophobic pockets characteristic of good small molecule binding sites, (3) cross reaction of small molecule compounds with cellular macromolecules other than the target can lead to unintended, and often clinically unacceptable, effects.

Methods for developing inhibitors of specific RNAs would be of great use in addressing the above limitations of small molecule therapeutics. This fact has not escaped notice; there have been a variety of attempts to develop therapeutic compounds that target RNA. Most of the effort has focused on non-small molecule compounds such as antisense oligonucleotides, peptide nucleic acid, ribozymes, DNAzymes and similar nucleic acid based compounds. These polymeric compounds do not have most of the advantageous pharmaceutical properties of small molecules. There are some preliminary reports of small molecule interactions with mammalian mRNAs, however these interactions are characterized by micromolar to millimolar affinities and do not appear generalizable.

As the molecular genetic description of disease advances, the level of specificity desired from therapeutic compounds increases as well. Current methods do not provide for the level of specific gene or allele inhibition required to treat many diseases. The limit of the discrimination problem is the need to distinguish allelic forms of RNAs or proteins that may differ by as little as one nucleotide or one amino acid. The value of being able to discriminate allelic differences is evident when one considers, for example, autosomal dominant diseases or diseases of excess gene dosage, where elimination of one mRNA (but not both) would have a therapeutic effect. There are no effective pharmaceutical methods for discriminating such closely related molecules.

A good example of a disease in which discrimination of allelic differences would be very helpful is Huntington's Disease, an autosomal dominant neurological disorder in which the presence of one copy of a Huntinton's allele (with an expanded triplet repeat) confers a gain of function phenotype associated with neurological dysfunction and degeneration. A variety of human and animal data support the view that elimination of the abnormal protein would eliminate the disease. However, once a protein is synthesized it is not clear that a small molecule can efficiently induce its prompt destruction. Therefore a more practical route is elimination of the RNA encoding the abnormal allele, thereby preventing synthesis of the abnormal protein. Prevention of such synthesis is advantageously performed at the RNA level, e.g., by promoting rapid destruction of the RNA, by preventing processing of pre-mRNA to mature mRNA preventing transport of mRNA from nucleus to cytoplasm, or preventing translation of mRNA to form protein.

A number of additional exemplary autosomal dominant diseases are shown in the following table. The information is also obtainable from other sources, for example at the electronic address shown below the table.

TABLE 1

Table of Autosomal Dominant Diseases

| OMIM Number[1] | Gene |
|---|---|
| 118100 | CERVICAL VERTEBRAL FUSION |
| 148210 | KERATITIS-ICHTHYOSIS-DEAFNESS SYNDROME |
| 601227 | PROGRESSIVE EXTERNAL OPHTHALMOPLEGIA, TYPE 3 |
| 601226 | PROGRESSIVE EXTERNAL OPHTHALMOPLEGIA, TYPE 2 |
| 600363 | SPASTIC PARAPLEGIA 6 |
| 157640 | PROGRESSIVE EXTERNAL OPHTHALMOPLEGIA |
| 173100 | PITUITARY DWARFISM DUE TO ISOLATED GROWTH HORMONE DEFICIENCY |
| 179800 | DISTAL RENAL TUBULAR ACIDOSIS |
| 193100 | VITAMIN D-RESISTANT RICKETS |
| 181350 | SCAPULOILIOPERONEAL ATROPHY WITH CARDIOPATHY |
| 182601 | SPASTIC PARAPLEGIA 4 |
| 182600 | SPASTIC PARAPLEGIA 3 |
| 166600 | TYPE II OSTEOPETROSIS |
| 146750 | ICHTHYOSIS, LAMELLAR |
| 601544 | NONSYNDROMIC SENSORINEURAL 3 DEAFNESS |
| 137600 | IRIDOGONIODYSGENESIS, TYPE 2 |
| 164500 | SPINOCEREBELLAR ATAXIA 7 |
| 156580 | MICROCEPHALY |
| 128100 | TORSION DYSTONIA 1 |
| 125310 | HEREDITARY MULTI-INFARCT TYPE DEMENTIA |
| 177850 | PSEUDOXANTHOMA ELASTICUM |
| 168601 | AUTOSOMAL DOMINANT LEWY BODY IN PARKINSON DISEASE |
| 600101 | DEAFNESS, AUTOSOMAL DOMINANT NONSYNDROMIC SENSORINEURAL 2 |
| 145410 | HYPERTELORISM WITH ESOPHAGEAL ABNORMALITY AND HYPOSPADIAS |
| 156590 | MICROCEPHALY WITH CHORIORETINOPATHY |
| 105650 | DIAMOND-BLACKFAN ANEMIA |
| 602485 | HYPERINSULINISM |
| 129490 | ECTODERMAL DYSPLASIA 3 |
| 601543 | NONSYNDROMIC SENSORINEURAL 8 DEAFNESS |
| 150250 | LARSEN SYNDROME |
| 104500 | HYPOPLASTIC LOCAL AMELOGENESIS IMPERFECTA 2 |
| 600666 | POLYCYSTIC KIDNEY DISEASE 3 |
| 164100 | NYSTAGMUS 2, CONGENITAL |
| 130050 | EHLERS-DANLOS SYNDROME, TYPE IV |
| 550000 | MITOCHONDRIAL DNA BREAKAGE SYNDROME, SECONDARY TO NUCLEAR MUTATION |
| 601251 | RETINAL CONE DYSTROPHY 2 |
| 169500 | AUTOSOMAL DOMINANT OR LATE-ONSET TYPE PELIZAEUS-MERZBACHER DISEASE |
| 134610 | FAMILIAL MEDITERRANEAN FEVER-LIKE SYNDROME WITH AMYLOIDOSIS |
| 193220 | VITREORETINOCHOROIDOPATHY |
| 601842 | AUTOSOMAL DOMINANT NONSYNDROMIC SENSORINEURAL 12 DEAFNESS |
| 142680 | FAMILIAL AUTOSOMAL DOMINANT PERIODIC FEVER |
| 600994 | AUTOSOMAL DOMINANT NONSYNDROMIC SENSORINEURAL 5 DEAFNESS |
| 177735 | PSEUDOHYPOALDOSTERONISM, TYPE I |
| 601369 | DEAFNESS, AUTOSOMAL DOMINANT NONSYNDROMIC SENSORINEURAL 9 |
| 161800 | NEMALINE MYOPATHY 1 |
| 174000 | MEDULLARY CYSTIC KIDNEY DISEASE 1 |
| 600223 | SPINOCEREBELLAR ATAXIA 4 |
| 603563 | SPASTIC PARAPLEGIA 8 |
| 144750 | HYPEROSTOSIS CORTICALIS GENERALISATA, BENIGN FORM OF WORTH, WITH TORUS PALATINUS |
| 600165 | NANOPHTHALMOS 1 |

[1] http//www.ncbi.nlm.nih.gov/Omim/

A second set of diseases in which allele specific inhibition would provide a therapeutic benefit includes cancer and other diseases with LOH. In these diseases there is a genetic difference between normal somatic tissues and disease tissues, and exploitation of that difference will provide a differential harmful effect on disease tissue compared to normal issue. The inhibitor molecules provided by this invention can also be used in such areas, as well as other applications where an inhibitor of an RNA would be beneficial, especially where an allele-specific inhibitor would be advantageous.

In accordance with the above description, as small molecules often have superior pharmacologic properties to polynucleotide therapeutics, there exists substantial interest in discovering ways to target specific RNA sequences and structures using small molecules. In a few limited examples, naturally occurring antibiotics have been found to act by binding the RNA component of ribonucleoprotein complexes, e.g., aminoaglycoside antibiotics. (Fourmy et al. (1996) Science 274:1367-1371) As such molecules cause global rather than gene-specific suppression of gene expression, their use has been limited almost exclusively to antibacterial and antifungal therapy. A more powerful and broad application of RNA targeting would entail the discovery of small molecules that bind specifically to particular RNAs or pre-mRNAs and modulate their function by, for example, inhibiting or activating translation or splicing. This is especially challenging because proteins are believed to displace all but the most strongly bound ligands from mRNA, and few if any small molecules are known to bind mRNA with an equilibrium dissociation constant ($K_d$) below 100 nM (Chow & Bogdan (1997) Chem. Rev. 97:1.489-1513). Nonetheless, at least one example exists to demonstrate that even micomolar RNA binders can specifically inhibit the expression of mRNA in cells (Mei et al. (1998) Biochemistry 37:14204-14212). Additionally, expression of a mRNA containing an engineered Hoechst dye-binding aptamer was found to be suppressed by addition of millimolar concentrations of dye to mammalian cells containing the engineered mRNA (Werstuck & Green (1998) Science 282:296-298). Notwithstanding these examples, it is widely recognized that RNA represents an especially difficult species to target using small molecules, as judged by numerous failures to discover legitimate leads in high-throughput screening efforts conducted throughout the pharmaceutical industry over the past decade. The difficulties in targeting RNA with small molecules most likely arise from the fact that highly structured RNAs present few hydrophobic pockets; in proteins, such pockets are almost without exception the binding sites for small molecules.

The current understanding of small molecule binding to macromolecules is largely shaped by the study of small molecule-protein interactions. The characteristics of such interactions include: (1) much of the binding energy is associated with the exclusion of water by hydrophobic contacts, typically involving an invagination of the protein surface (hydrophobic binding pocket) into which the small molecule ligand fits; (2) The binding often entails some change in the orientation of the amino acids comprising the pocket (induced fit); (3) charge interactions are generally not a component of high affinity protein—small molecule interactions.

These properties of small molecule-protein interactions indicate that RNA are targetable by small molecules as well because RNA shares many of the properties of proteins that make them attractive for binding small molecules. First, RNA frequently adopts a shape similar to proteins that bind small molecules. Second, the surfaces of RNAs tend to present, the sugars and bases, thereby facilitating interactions of these groups with small molecules. Such interactions can include hydrogen bonding, van der Waals interactions, and electrostatic interactions, as well as hydrophobic interactions in certain orientations. Third, like proteins, RNA structures are plastic, which allows them to mold to the shape of a ligand (induced fit). Fourth, the sequence complexity of RNA, and particularly the complexity of higher order RNA structure, creates unique three dimensional structures in specific RNAs that are targetable with high specificity.

Despite these attractive properties of RNAs, the development of small molecule inhibitors of RNA has not advanced beyond the identification of some natural products (aminoglycoside antibiotics) which bind prokaryotic ribosomal RNA and inhibit protein translation. The reasons for this include: the hydrophobic surfaces of RNA exist amidst a high concentration of polar (edges of bases, 2'-OH groups of sugars) and charged (phosphate moieties) groups which are repulsive to hydrophobic moieties. Thus it is not surprising that most small molecules that bind RNA have charged functionality in addition to hydrophobic surfaces. These are, the characteristics of aminoglycoside antibiotics, for example. The charge on such molecules impedes cell membrane penetration and generally confers upon such molecules poor pharmacological properties (e.g. poor intestinal absorbtion, poor binding to serum proteins that act as carriers).

An important aspect of the present invention is the realization that the formation of a trimolecular complex between an RNA, a protein and a small molecule can address some of the limitations of small molecule—RNA interactions. In particular, favorable electrostatic contacts between a protein and an RNA can dissipate charge, thereby creating an improved local environment for hydrophobic interactions between the RNA binding moiety of a small molecule and its target RNA. There is also a cooperative quality to the binding interactions between (1) RNA and protein, and (2) the small molecules of this invention, which link an RNA and a protein via interactions with two moieties of the small molecule.

The favorable electrostatic interactions between protein and RNA which are an aspect of this invention will depend on the specific chemical characteristics of the target RNA and the target protein. Such interactions are understood by those skilled in the art. It is worth noting, however, that most proteins have a preponderance of polar and charged residues on their surfaces, and proportionately fewer hydrophobic groups. Further, many proteins have patches (in three dimensional space) of basic residues in the vicinity of their ligand binding sites. Such proteins would constitute one class of preferred protein partners for the small molecules of this invention.

Thus, the description presented here provides a way to overcome the weak interactions that are characteristic between small molecules and RNA, and can provide a mechanism for small molecules to bind to and alter the biology of a specifically targeted RNA. As indicated above, in a general aspect, this invention includes a RNA target, a cellular protein, and a small molecule that simultaneously interacts with both the RNA and the protein bringing them into close proximity. An important aspect of the invention is that the protein and the RNA, when in close proximity, also interact, but only when brought together through the intermediacy of the small molecule. In other words, the RNA and the protein do not appreciably interact in the absence of the small molecule. The resulting trimolecular complex (protein-small molecule-RNA), initiated by the small molecule, provides a level of stability that would be difficult to achieve with the small molecule alone, because the ensuing protein-RNA contacts stabilize the overall complex. Harnessing "additional" RNA binding affinity by recruitment of cellular protein, can result in a binding complex with increased affinity for the targeted RNA. The result of complex formation can be to prevent translation, to shorten mRNA half-life, or to induce mRNA cleavage, thereby suppressing expression of the targeted gene.

Thus, the close juxtaposition of protein and RNA would drive RNA-protein interactions that would not otherwise occur. Therefore, the protein that is recruited by the small molecule to form the RNA binding complex need not necessarily be limited to RNA binding proteins. Proximity can also induce RNA-protein interactions even involving proteins that are not known to bind RNA with high affinity or high specificity. The interactions with RNA may occur by exploiting amino acids normally involved in protein-protein interactions or basic residues that are positioned close to the RNA. The resulting trimeric complex would have specificity (due to the small molecule) and high affinity (due to multiple synergistic binding interactions with RNA of both the small molecule and protein). Proteins that would be advantageous for use in this invention include:

Abundant proteins (so that protein constituent of complex would not be limiting)

Ubiquitously expressed proteins (so that method can be applied to all target tissues)

Proteins with known small molecule ligands (simplifies method and likely provides increased affinity of the protein-RNA interaction component of the trimer complex)

DNA binding proteins

Ribonucleases (Rnases) (shorten half-life of targeted RNA, suppressing translation and gene expression, does not rely on steric interactions to prevent translation)

Proteins that bind cell-permeable small molecule ligands

A method to enhance the bioactivity of RNA-binding small molecules is described. This method is predicated on: (1) identification of a cellular protein with favorable characteristics to interact with RNA if brought in close proximity; (2) synthesis of a bipartite small molecule possessing an invariant ligand on one end that interacts with the identified protein and a variable structure (e.g., generated by combinatorial chemistry) on the other end; and (3) an assay able to detect specific binding of the protein-small molecule composite surface to the targeted RNA.

General techniques for regulating the proximity and orientation of proteins in cells have been developed (Schreiber & Crabtree (1996) Trends Biochem. Sci. 21:418-422) and are relevant and useful for this invention. Small molecule chemical inducers of dimerization (CIDs), which bind two proteins simultaneously, have been used to modulate the activity of several different cellular protein, interactions (developed (Schreiber & Crabtree (1996) Trends Biochem. Sci. 21:418-422; Spencer et al. (1993) Science 262:1019-1024; Pruschy et al. (1994) Chem. Biol. 1:163-172; Spencer et al. (1996) Curr. Biol. 6:839-847; Belshaw et al. (1996) Chem. Biol. 3:731-738; Spencer et al. (1995) Proc. Nat. Acad. Sci. USA 92:9805-9809; Holsinger e al. (1995) Proc. Nat. Acad. Sci. USA 92:9810-9814; Luo et al. (1996) Nature (London) 383: 181-185; Farrar et al. (1996) Nature (London) 383:178-181; Belshaw et al. (1996) Proc. Nat. Acad. Sci. USA 93:4604-4607; Harding et al. (1989) Nature (London) 341:758-760) and show the feasibility of enlisting non-physiological interactions to effect physiological changes.

One such CID, rapamycin, binds both FK506 binding protein (FKBP12) and FKB12-rafamycin-associated protein (FRAP) simultaneously, creating a trimeric complex. Complex formation inhibits the kinase activity of FRAP, resulting in cell cycle arrest at $G_1$. Interestingly, it is the composite surface, with contributions from both rapamycin and FKBP12 which mediates the interaction of the complex with FRAP. The X-ray crystal structure for this trimeric complex has been solved (Choi et al. (1996) Science 273:239-242). The structure shows that the rapamycin is a bipartite molecule interacting with a hydrophobic pocket on each protein. Each end of rapamycin fits into each protein allowing alignment and protein-protein interaction to the two bound proteins to occur. Although rapamycin interacts extensively with both protein partners, the extent of protein interaction is limited. The structure suggests that the interaction does not require extensive protein interactions, because only 3H-bond contacts and only 400 $Å^2$ of solvent-accessible surface area participate in the interaction between FRBP12 and FRAP.

The present invention involves targeting a mRNA sequence, a mRNA variance, or a structural variation due to a nucleotide variance with a small molecule. This can be achieved using a relatively low affinity RNA-binding small molecule whose binding is augmented by being presented to the RNA as a complex with a protein. To form high affinity complexes with RNA, usually a bipartite small molecule is designed to include an invariant protein-specific ligand on one end and an element of a combinatorial small molecule library on the other end, connected by a linker. The bipartite small molecule will bind to its protein and create a composite binding surface that would interact with RNA. With binding moieties and linker, properly selected, "protein highjacking" by the small molecule will induce the formation of protein-RNA bonds that would otherwise not occur, resulting in high affinity binding to the target RNA. The stability of the complex (mRNA, small molecule, and protein) will be higher than the binding of either of the components to the target mRNA individually and could alter the biology of the target mRNA.

In a specific application, a protein-small molecule complex is created by binding of a specific protein to the invariant specific ligand on one end of the bipartite small molecule. Preferably this protein would bind the small molecule in a hydrophobic pocket that was surrounded with basic residues favoring interaction with nucleic acid. The binding would result in a composite binding surface whose characteristics would be contributed by the local amino acid residues and the particular chemical entity presented by the variable end of the small molecule. The dimeric complex would then be assayed for RNA binding to identify potential chemical inducers of protein-RNA dimerization. By analogy to the system described for CIDs, the juxtaposition of both macromolecules by the small molecule will induce RNA-protein interactions resulting in a high affinity trimolecular complex. High affinity complex formation can result in an alteration of the biology of the mRNA and suppression of gene expression. This can occur in at least two ways:

1) If the complex were to form in the 5' UTR, 3' UTR, splicing junctions of mRNA, or the coding region of the mRNA, the stability of the complex could inhibit maturation, processing, or translation of the mRNA.
2) If the "highjacked" RNA binding protein also contains a nuclease activity (e.g., RnaseL), then the trimerization could direct specific cleavage of the target mRNA.

RnaseL represent one potential candidate nuclease whose binding could be strengthened in the presence of the appropriate small molecule. RnaseL is unique among nucleases in that its activity is ligand dependent. A ligand binding domain has been identified in the amino terminal region of this nuclease which, when bound with ligand, activates the nuclease activity of the protein. This domain and its characterized ligand, 2'-5' oligoadenylate (2-5A), present a blueprint upon which to model a bipartite small molecule that would bind to RnaseL, both activating its nuclease activity and targeting it to a specific RNA simultaneously. For this application, a specific bipartite small molecule would be synthesized with a 2-5A ligand mimic at one end and elements of a combinatorial library at the other end. The action of the modified small molecule would take place in two stages: 1) recognition of and binding to RnaseL; 2) recruitment and local activation of RnaseL to ablate the target mRNA.

Other RNases could also be used, with or without engineering of ligand-dependent nuclease activity, as well as other RNA binding proteins. Such proteins have the advantage that the structure is known to be suitable for forming a stable complex with RNA, thus it is very probable that that stability can be utilized in forming a specific protein-small molecule-RNA complex. The structure can be modified as desired to provide a suitably low level of non-specific RNA binding. Those skilled in the art are familiar with the modification and mutation methods useful for modifying protein structure and evaluation of the resulting RNA binding properties, and further with how to provide a suitable balance between RNA binding in the absence of the small molecule and stabilization of the complex.

Those skilled in the art also recognize that identification of binding small molecules, and the particular binding moieties, which can simultaneously bind to a selected protein and a target RNA can proceed in various ways, all of which are within the scope of this invention. While it is preferred that screening for binding occur with small molecules which contain a first and second potential binding moieties and a linker joining the two, a binding molecule can also be constructed by building up from an initial binding molecule. Thus, for example, a small molecule can be identified (e.g., by screening or by identification of a known ligand or binding compound) which binds to the selected protein. This molecule can be used as the first moiety and attached to a variety of linkers and/or attached to the linker with various chemistries or attachment locations. The combined first moiety and linker molecules can then be screened to identify those which retain binding capability. Those which retain binding can then be attached to potential RNA binding moieties and screened for binding to the target RNA, either in the presence or absence of bound protein. Similarly, the build-up could proceed from the RNA binding moiety and/or could begin with one of the moieties attached to linker(s). In any of the approaches, it can be beneficial to vary the linker (e.g., different linker molecules and/or different length linkers) to identify molecules with better characteristics (e.g., tighter binding).

Additional information on the construction of small molecule libraries and the selection of the first and second moieties and linkers of the described complex-forming compounds follows.

Protein Binding Moiety—Moiety 1

In one embodiment of the invention the selection of a protein binding moiety (moiety 1) is achieved by a screening process. The aim of the screening process may be to identify a ligand for a protein that does not have a known small molecule ligand, or to optimize a known ligand. For example, the protein RNAse L has a known ligand, 2'-5' oligoadenylate (2-5A), however it may be desirable to identify a smaller, or less charged molecule that interacts with the 2-5A binding site of RNAse L. Such a molecule can be identified by a screening assay in which RNAse L is fixed in the well of a microtiter plate and tested for binding (and, optionally, activation of RNAse activity) by a series of 2-5A analogs. One skilled in the art will recognize that nucleotide analogs, or oligomerized nucleotide analogs (with modification of the phosphodiester bond, the sugar, the base, or some combination of these groups) would be a useful starting point for such a library, however other approaches are also useful, such as non-nucleotide structures which replicate some of the structural elements of 2'-5' polynucleotides. Alternatively, a synthetic or natural product library can be screened without respect to the structure of the natural ligand.

In general the composition of a library from which to select a binding moiety 1 should be guided by the principles which inform design of small molecule libraries for protein targets. Guidance on the construction of such libraries is provided in a number of recent texts including the following. Terrett, N. K. and Terret, N., (1998) *Combinatorial Chemistry* (Oxford Chemistry Masters) Oxford Univ Press, ISBN: 0198502192. Terrett, Nicholas K. (1998) *Combinatorial Chemistry* (Oxford Chemistry Masters, 2), Oxford Univ Press, ISBN: 0198502206. Wilson, Stephen R. (Editor), and Anthony W. Czarnik (Contributor) (1997). *Combinatorial Chemistry: Synthesis and Application*, John Wiley & Sons, ISBN: 047112687X. Bunin, Barry A. (Editor) (1998) *The Combinatorial Index*, Academic Press, ISBN: 0121413403. Obrecht, Daniel and Jose M. Villalgordo (1998) *Solid-Supported Combinatorial and Parallel Synthesis of Small-Molecular-Weight Compound Libraries* (Tetrahedron Organic Chemistry Series, V. 17), Pergamon Press, ISBN: 0080432581.

In another aspect of the invention the protein binding moiety is a known small molecule ligand of a cellular protein or an analog of such a ligand. Examples of specific small molecules which may be useful for moiety 1 include: adenosine triphosphate analogs, which could sequester one or more cellular ATPases; flavin adenine dinucleotide or FAD analogs; nicotinamide or nicotinamide analogs; folates or folate analogs, which could sequester proteins such as dihydrofolate reductase, thymidylate synthase or other abundant proteins which require folate as a cofactor; cyclosporin, FK506, rapamycin, and coumermycin or their synthetic analogs, which bind to FK506 Binding Protein (FKBP). Dimerization schemes based on the latter four natural products have been described. Recently totally synthetic, cell-permeable analogs of these compounds, with superior pharmacological properties, have been produced. (Amara, J. F., Clackson, T., Rivera, V. M., Guo, T., Keenan, T., Natesan, S., Pollock, R., Yang, W., Courage, N. L., Holt, D. A. and M. Gilman (1997) *Proc. Natl. Acad. Sci. U.S.A.* 94(20):10618-23.). The compounds of Amara et al. are also useful compounds for the present invention.

Another class of known ligands of cellular proteins are ligands for nuclear proteins. Such ligands have the advantage of providing access to pre-mRNA, which is confined to the nucleus. Pre-mRNA, which includes introns of intron-containing genes, is often larger than processed mRNA, and therefore contains more potentially targetable structures. Ligands of nuclear proteins include nucleotide analogs which bind to specific DNA repair proteins. Examples of such ligands include 5' fluorocytidine, which binds to DNA methyltransferase; $^6$O-benzylguanine, which binds methylguanine DNA methyltransferase; and alkylated ethenoguanine, which binds to alkyladenine DNA glycosylase.

Another class of ligands which bind cellular proteins are amino acid analogs which bind proteins involved in amino acid metabolism or protein translation. Examples of such molecules include borrelidin, which binds histidyl tRNA synthetase, and histidinol, which binds histidyl tRNA synthetase, as well as the L-glutamine antagonists acivicin, DON and azaserine; the aspartic acid analogs PALA and L-alanosine, as well as compounds such as buthionine sulfoximine and difluoromethylornithine.

Any of the enumerated ligands, as well as others, could serve as the starting point for generating a library with the composition: moiety 1 (fixed ligand)+moiety 2 (library), or the composition: moiety 1 (fixed ligand)+linker (fixed or library)+moiety 2 (library). Alternatively any of the ligands mentioned could be used as the basis for constructing a library of limited diversity in order to identify a more advantageous ligand for the selected cellular protein.

In another aspect of the invention a preferred size for moiety 1 is less than 1,500 Da, a still more preferred size is less than 1,200 Da, a still more preferred size is less than 900 Da and a most preferred size is less than 600 Da.

RNA Binding Moiety—Moiety 2

The RNA binding moiety is in general any moiety with desirable chemical and pharmaceutical properties which binds to a specific target RNA with high affinity. Such a moiety may be identified from a combinatorial small molecule library or a natural product library by a screening assay of the type described below. A preferred moiety 2 is a molecule which can participate in hydrophobic interactions with RNA.

In another aspect of the invention a preferred size for moiety 2 is less than 1,500 Da, a still more preferred size is less than 1,200 Da, a still more preferred size is less than 900 Da and a most preferred size is less than 600 Da.

Linker Moiety

As indicated above, a linker moiety is optional. However, in specific instances the linker moiety will be an essential element of the small molecule library, and in particular may be important for bringing the target mRNA and protein together in optimal orientation and at an optimal distance. There may be one, two or more linkers joining moieties 1 and 2, depending on the structure of moieties 1, and 2 and the optimal geometry for the trimolecular complex. In preferred embodiments there is one linker. Examples of useful linker chemistries are provided, without limitation, in FIG. 5.

Linker groups may be varied to achieve different orientations or different distances between moieties 1 and 2. For example, the linker group may include a planar aromatic ring system (see diagram) such as, for example, a benzene ring. Moieties 1 and 2 may be attached to the ring or rings in any of the possible orientations, some of which are indicated in the figure. Alternatively linkers may consist of hydrocarbon chains of various lengths and chemical compositions. Several exemplary hydrocarbon chains are shown in the figure, along with some of the possible points of attachment for moieties 1 and 2. Another possible linker moiety is a substituted sugar or polysaccharide. Exemplary sugars are shown in the figure, along with some possible sites for attaching moieties 1 and 2. Another possible linker moiety is a beta lactam or cepham ring. Examples of such rings are shown in the figure, along with some possible sites for attaching moieties 1 and 2. Yet another possible linker is an amino acid, an amino acid analog or a short chain of amino acid analogs. One skilled in the art will recognize that the exemplary linker structures provided are not comprehensive, and that additional variations on the structures shown, as well as the use of other organic chemical groups of similar size may be useful to achieve other orientations or distances between moieties 1 and 2.

It may be useful to join certain moieties 1 and 2 at more than one site; that is, it may be useful in some instances to use more than one linker. In such cases either both or all linkers may be of the same type, or one linker may of one type and the second or more linkers may be of another type or types. Linker types include not only those listed above but other structures that will be evident to one skilled in the art.

Although the linker moiety is intended to join moieties 1 and 2, another aspect of this invention is the participation of the linker in contacts with either moiety 1 or moiety 2. For example, sugars are known to be capable of binding RNA. Thus, in some cases, contacts between a substituted sugar and either moieties 1 or 2 may contribute to the affinity or stability of the trimolecular complex.

In another aspect of the invention a preferred size for moiety 2 is less than 700 Da, a still more preferred size is less than 500 Da, a still more preferred size is less than 400 Da and a most preferred size is less than 300 Da.

Screening Assays

Screening the small molecule libraries of this invention can take place in several ways. For example, first, one can hold constant the composition of moiety 1 and a linker and create a library which varies only at moiety 2. Alternatively just moiety 1 is fixed and the library is made by varying the linker and moiety 2. These same two approaches can be taken with moiety 1 and 2 reversed. Once a ligand is selected at one moiety, for example moiety 2, it may be useful to create a constrained library with moiety 2 and the linker fixed and moiety 1 only varying to a limited degree, so as to explore the effects of the selected moiety 2 on the binding of moiety 1 (even if moiety 1 has been previously selected). Similar experiments can be performed in which both the linker and moiety 1 are varied. The same libraries and screens can be performed with moieties 1 and 2 reversed.

In one aspect of the invention the linker is the preferred component of the library to vary having selected a moiety 1 and a moiety 2. The reason is that the apposition of protein and RNA surfaces in the optimal spatial relationship will be crucial to achieving the maximal possible binding affinity. This optimal relationship will entail maximizing attractive electrostatic interactions while allowing for maximal hydrophobic contacts by the protein. One skilled in the art will recognize that the permutations of linker composition and structure enumerated above are only a fraction of the structures that could be used to bring moieties 1 and 2 into optimal alignment.

Once a library is made it can be screened in several ways. First, a library can be screened for binding to its intended target. For example, a library in which moiety 1 varies can be screened for binding to the target protein, or a library in which moiety 2 varies can be screened for binding to the target RNA. One convenient assay for such screens is the scintillation proximity assay (SPA). In this assay a radioactive isotope and a scintillant are brought into proximity by a specific binding interaction, allowing the radioemitter to excite the scintillant, which is then detected with sensitive detectors. This arrangement obviates the need to separate free from bound components, and allows real time monitoring of the binding interaction. SPA can be carried out more rapidly than most other methods used to monitor binding reactions, and is also relatively inexpensive. The methodology also lends itself to automation. (For a review of the SPA see: Udenfriend, S., Gerber, L. and Nelson, N. (1987) Scintillation proximity assay: a sensitive and continuous isotopic method for monitoring ligand/receptor and antigen/antibody interactions. *Anal Biochem* 161(2):494-500. For an up to date review of automated high throughput screening see: Fernandes, P. B. (1998) Technological advances in high-throughput screening. *Curr Opin Chem Biol* 2(5):597-603.)

An alternative assay format is to screen a library in the presence of both the target RNA and the target protein. This allows the affinity of the final complex to be assessed.

Another useful assay is to screen a library in the presence of both the target RNA and the target protein present in a cell extract which contains substantially all the other cellular constituents which might interact with the target RNA, the target protein or the small molecule.

A final important assay is to screen a library in the presence of cells which express both the target RNA and the target protein, and where there is an assay for abrogation of RNA function.

In addition to the provision of particularly advantageous molecules which can be used to inhibit an activity or activities of specific cellular RNA molecules, the invention is also concerned with the identification and use of targets within and RNA sequence, which are particularly useful for allele specific inhibition of an activity of RNA corresponding to a particular gene. In general, these targets are related to changes in secondary structure of an RNA species which occur as a result of the presence of one or more sequence polymorphisms in an RNA (i.e., differences in secondary structure between allelic forms of an RNA, especially an mRNA or a pre-mRNA. Commonly, the sequence polymorphisms are Single Nucleotide Polymorphisms (SNPs).

SNPs are single base-pair substitutions that occur within and outside genes (1-3). Due to the growing recognition that SNPs can be used as genetic markers for identifying genes that contribute to disease susceptibility or resistance (4, 5), or drug response (6, 7), SNP discovery has been markedly accelerated over the past two years. Within intragenic regions composed of introns and exons, the average frequency of SNP occurrence is approximately 1 in every 500 base pairs, with introns more highly variable than exons (2). Within exons, SNPs occur in both protein-coding regions and the 5'- or 3'-UTR regions, and those in coding regions do not always cause amino acid variations.

Genes containing one or more SNPs can give rise to two or more allelic forms of mRNAs. SNPs associated with different allelic forms of mRNA may account for allelic variation in the interaction of mRNA with cellular components involved in its synthesis, maturation, transport, translation or degradation. It has been documented that a number of single base-pair substitutions alter or create essential sequence elements for splicing, processing or translation of human mRNA (1). These SNPs exhibit phenotypic consequences including altered length and/or steady-state level of cytoplasmic mRNA. On the other hand, SNPs that do not affect RNA consensus and protein sequences have not been analyzed in detail. It is conceivable that such SNPs could also lead to variant phenotypic effects, most likely through non-consensus-dependent mechanisms.

It has been shown by a growing body of evidence that the folding of mRNA influences a diverse range of biological events such as mRNA splicing (8, 9) and processing (10-12), and translational control (13-16) and regulation (17-19). Since the structure of mRNA is determined by its nucleotide sequence and its environment, we were interested to examine whether the folding of mRNA could be influenced by the presence of SNPs. In this report, we describe the analysis of two previously identified SNPs in coding regions (V. P. Stanton, Jr., unpublished results): a U/C transition at nucleotide 1013 of human alanyl tRNA synthetase (AARS, GenBank Accession # D32050) and a U/C transition at nucleotide 1674 of human replication protein A, 70 kDa subunit (RPA70, GenBank Accession # M63488). Both SNPs do not affect amino acid sequences of the respective proteins. An initial screen of lymphoblasts from 36 unrelated individuals (V. P. Stanton, Jr., unpublished results) revealed that heterozygotes that carry both the U- and the C-alleles and homozygotes that carry only one of the two alleles occur at frequencies of 57% and 43%, respectively, for AARS, mRNA; and 31% and 69%, respectively, for RPA70 mRNA. Using structural mapping and structure-based targeting strategies, we show that the SNPs have, profound effects on the structural folds of the mRNAs. Such findings of the contribution of common genetic variation to structural diversity of mRNA have not been described previously. These results suggest that phenotypic consequences of SNPs could arise from mechanisms that involve allele-specific structural motifs in mRNA.

The targets identified as corresponding to sequence polymorphisms are, in particular, useful for targeting (including screening and inhibitory use) with the complex-forming molecules described herein. However, the use of those targets is not limited to targeting with such molecules, but rather can be targeted using any type of allele specific inhibitors (see e.g., Housman, supra).

Likewise, the complex-forming molecules described herein are useful for targeting to the targets corresponding to RNA secondary structure, but their use is not limited to those targets. Instead, such molecules can be used for any target in an RNA for which specific binding molecules are developed.

Thus, the present invention provides targets and inhibitory molecules which are broadly applicable for treatment of diseases in which inhibition of a particular RNA would be beneficial, e.g., autosomal dominant diseases, proliferative disorders such as cancer, and diseases where reduction of expression of a gene would be helpful.

As understood by those skilled in the art, inhibition of an RNA or treatment of a disease in a patient can be performed in many different ways, depending in part on the particular characteristics of the disease and of the molecule to be delivered or administered. Guidance on preparation and administration of therapeutic compounds and pharmaceutical compositions is provided in the following section.

Preparation & Administration of Pharmaceutical Compositions

For the treatment of patients suffering from a disease or other condition in which the inhibition or other modulation of an RNA is desired, the preferred method of preparation or administration will generally vary depending on the type of compound to be used. Thus, those skilled in the art will understand that administration methods as known in the art will also be appropriate for the compounds of this invention.

The particular compound that exhibits activity on a target RNA can be administered to a patient either by itself, or in pharmaceutical compositions where it is mixed with suitable carriers or excipient(s). In treating a patient exhibiting a disorder or condition of interest, a therapeutically effective amount of an agent or agents is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedure's in cell cultures and/or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. Such information can be used to more accurately determine useful doses in humans. Levels in plasma may be measured, for example, by HPLC or other means appropriate for detection of the particular compound.

The exact formulation, route of administration and dosage can be chosen by the individual physician in view of the patient's condition (see e.g. Fingl et. al., in *The Pharmacological Basis of Therapeutics,* 1975, Ch; 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With, proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

As described in the Examples below, we have demonstrated that a single nucleotide polymorphism can cause dramatic structural variation in allelic forms of human mRNA. The structural differences occur both at and in regions flanking the SNP. The structural differences allow allele-specific cleavage of mRNA with oligonucleotides complementary to a site of maximum differential structural accessibility that is independent of single base discrimination at the polymorphic site. These findings are of particular interest in several respects. First, the results illustrate how SNPs can affect mRNA structure, and suggest mRNA-structure-dependent mechanisms by which SNPs can cause allele-specific biological consequences. Further elucidation of the contribution of common genetic variation to structural and functional diversity of mRNA will provide insight into fundamental mechanisms of human phenotypic variation, and facilitate studies of disease susceptibility and drug response (4-7). Second, the results described here caution researchers to consider the effect of genetic variation in their characterization of RNA as a therapeutic target. Lastly, our novel strategy of allelic structure-based mRNA targeting may be applied to therapeutic allele-specific RNA down-regulation, preferably in the 5'- and 3'-UTR regions, using other types of specific RNA binders such as small molecule inhibitors (30-32) to allow enhanced cellular uptake and improved allele discrimination.

Example 1

In vitro Synthesis and Purification of mRNA. Human cDNAs for PCR synthesis of transcription templates were prepared from total RNA of Epstein-Barr virus (EBV) transformed lymphoblasts (Coriell Institute) or tumor cell line NCI-H292 (American Type Culture collection). The cDNAs were genotyped for SNPs in human AARS and RPA70 either by sequencing or by restriction fragment length polymorphism (RFLP) analysis. A second round cDNA sequencing was performed to confirm the nucleotide sequence of AARS and RPA70 cDNAs. Fragments of human mRNA alleles (113-1000 mers) varying in a single base were obtained by in vitro transcription from PCR derived DNA templates using Megashortscript or Megascript T7 kits (Ambion). Crude transcripts were either purified on an 8% denaturing polyacrylamide gel or on a G-50 sephadex spin column (Boehringer Mannheim), and the purified mRNA was subsequently dephosphorylated using calf intestinal alkaline phosphatase (Pharmacia) and 5'-end-labeled with $^{32}P$ using $[\gamma$-$^{32}P]ATP$ (DuPont NEN) and T4 polynucleotide kinase (Pharmacia).

Example 2

Enzymatic Mapping of Allelic mRNA Structures. Partial digestion of 1 pmol of 5'-$^{32}$P-labeled allelic mRNA by nuclease S1 or RNase T1 (Pharmacia) was carried out at 37° C. for 5 min in 10 µL buffer containing 10 mM Tris.HCl, pH 7.5, 100 mM KCl, 5 mM $MgCl_2$, and 5 µg phenol-extracted glycogen. Prior to the addition of S1 or T1, the RNA was renatured in the assaying buffer by heating for 45 sec at 85° C., then cooling for 5 min at room temperature followed by 10 min at 37° C. The digestion products were fractionated on either a 4, 6 or an 8% denaturing polyacrylamide gel, and the cleavage patterns visualized by autoradiography. RNase T1 digestion at 55° C. and alkaline hydrolysis at 85° C. were done to generate sequence ladders for cleavage site identification. RNase T1 digestion at 55° C. was done for 1 min in 15 µL buffer containing 25 mM sodium acetate, pH 5.2, 25 mM KCl, and 3 µg yeast tRNA. Alkaline hydrolysis was done for 15 min in 15 µL buffer containing 50 mM sodium bicarbonate, pH 9.2, 1 mM EDTA, and 10 µg phenol-extracted glycogen.

Example 3

*E. coli* RNase H Digestion Assay. Phosphorothioate oligodeoxyribonucleotides (PS-oligos) were employed in our studies because of their enhanced stability against nucleases (20). PS-oligos were chemically synthesized and desalted on C-18 cartridges by Synthetic Genetics. One, pmol of 5'-$^{32}$P-labeled mRNA was renatured in 12 μL RNase H buffer (20 mM Tris.HCl, pH 7.5, 10 mM KCl, 5 mM MgCl$_2$, 0.1 mM dithiothreitol (DTT), 5% glycerol, and 10 μg phenol-extracted glycogen) by heating for 1 min at 85° C., then cooling for 5 min at room temperature followed by 10 min at 37° C. *E. coli* RNase H (0.6 units, Pharmacia) was then added to the renatured mRNA and incubated for 5 min at 37° C. PS-oligos (5 pmol in RNase H buffer) were subsequently added, and the reaction mixture (15 μL total) incubated for 20 min at 37° C. The digestion products were fractionated on a 4% denaturing polyacrylamide gel, and the cleavage patterns visualized by autoradiography. RNA levels were quantified using a phosphoimager (Fujifilm Model FLA-2000).

Example 4

Oligonucleotide-directed Cleavage of Endogenous RPA70 mRNA in Human Cell Extracts. Human tumor cell lines HeLa and Calu-1 (American Type Culture collection) were genotyped for SNPs in RPA70 cDNA by RFLP analysis and by sequencing. The genotyping results showed that HeLa and Calu-1 express only the U- or the C-base at the 1674U/C polymorphism, respectively. HeLa cells were cultured in monolayers in minimum essential medium (Gibco BRL), and Calu-1 cells were cultured in monolayers in McCoy's 5A medium (Sigma). Both media were supplemented with 10% heat inactivated fetal bovine serum (JRH Biosciences), 100 units/mL penicillin-100 μg/mL streptomycin (Gibco BRL), and 2 mM L-glutamine (Gibco BRL). Both cell lines were grown under 5% CO$_2$/95% air in a humidified incubator at 37° C. For preparation of cell extracts, the cells were grown to 80-90% confluence, typsinized, and washed twice with the complete medium as specified above and twice with phosphate buffered saline (Gibco BRL). Approximately 5×10$^7$ Cells were lysed in a 15 mL tissue grinder with a Teflon pestle (Wheaton) in the presence of 1.5 mL lysis buffer (20 mM Tris.HCl, pH 7.5, 420 mM NaCl, 2 mM MgCl$_2$, 0.2 mM EDTA, 1 mM DTT, 0.5 mM phenylmethyl sulfonylfluoride (PMSF), and 25% glycerol). The sodium salt concentration was chosen to facilitate the disruption of the nuclear membrane to release RNase H from nuclei (21). Up to 200 strokes were needed to completely lyse the cells, as checked using a hemacytometer. The cell lysate was centrifuged at 14,000, rpm for 10 min at 4° C., and cell extracts were obtained by transferring supernatant to clean microcentrifuge tubes and freezing immediately at −80° C. Total protein concentration of cell extracts was determined using the Bradford assay (Bio-Rad). For oligodeoxynucleotide-directed cleavage of endogenous mRNA reactions, cell extracts were diluted to a total protein concentration of 3 mg/mL with the lysis buffer. After the addition of a 10× PS-oligo solution to the diluted cell extracts, the reaction mixture was incubated for 40 min at 37° C. The level of intact RPA70 mRNA was determined by total RNA isolation and Northern blot hybridization using procedures described previously (22, 23), and followed by phosphoimager analysis. Northern probes specific for RPA70 mRNA were synthesized by random primed [α-$^{32}$P]dCTP-labeling of a cDNA probe corresponding to nucleotides 1519-2080 of human RPA70 mRNA. To account for variability in the amount of total RNA loaded into individual gel wells for Northern analysis, the level of glyceraldehyde 3-phosphate dehydrogenase (GAPDH) mRNA was also measured by first stripping the RPA70 mRNA probe, and then reprobing the same Northern blot with a random primed [α-$^{32}$P]dCTP-labeled cDNA probe corresponding to a 600 nucleotide sequence of human GAPDH (Stratagene).

Example 5

Characterization of SNP-containing mRNA Structures. Two SNPs in the coding regions of two human mRNAs were analyzed in this study: a U/C transition at nucleotide 1013 of human alanyl tRNA synthetase (AARS, GenBank Accession # D32050)) and a U/C transition at nucleotide 1674 of human replication protein A, 70 kDa subunit (RPA70, GenBank Accession # M63488)). To investigate effects of these SNPs on mRNA structure, we first synthesized both allelic SNP-containing fragments of the two mRNAs by in vitro transcription and, then performed mRNA structural mapping using structure-specific enzymes RNase T1 and/or nuclease S1.

Nuclease S1 cleaves both DNA and RNA in single-stranded regions (24, 25). It is a useful structural probe for identifying large unpaired accessible regions (>4 nucleotides) in RNA. FIG. 1*a* shows nuclease S1 mapping of a 113-nucleotide fragment of AARS mRNA (nucleotides 951-1063). Differences in S1 cleavage patterns were observed between the U- and the C-alleles. Strong cleavages centered at nucleotide 999 of the U-allele revealed the presence of a single-stranded region approximately 14 nucleotides upstream of the SNP. The majority of the species of the C-allele lack such a single-stranded region, as shown by the absence of strong cleavage bands in the same region. Allelic differences in S1 accessibility were also observed at several other sites including regions 980 and 1032 (FIG. 1*a*). At higher S1 concentrations both alleles exhibited similar cleavage patterns at sites 980 and 1032, suggesting that the stronger cleavage intensities at these sites in the C-allele may be due partly to the absence of a large unpaired region at position 999. Structural mapping by RNase T1 (data not shown), which identifies unpaired guanosine residues (25), corroborated the finding of substantial allelic structural differences within ±14 nucleotides of the SNP. The enzymatic mapping experiments were also done on a 1000-nucleotide fragment (nucleotides 529-1528) of the AARS mRNA. Differential S1 digestion patterns of the two alleles identical to those at sites 980, 999 and 1032 in FIG. 1*a* were observed with the 1000-mer mRNA sequence (data not shown).

Figure 1B:
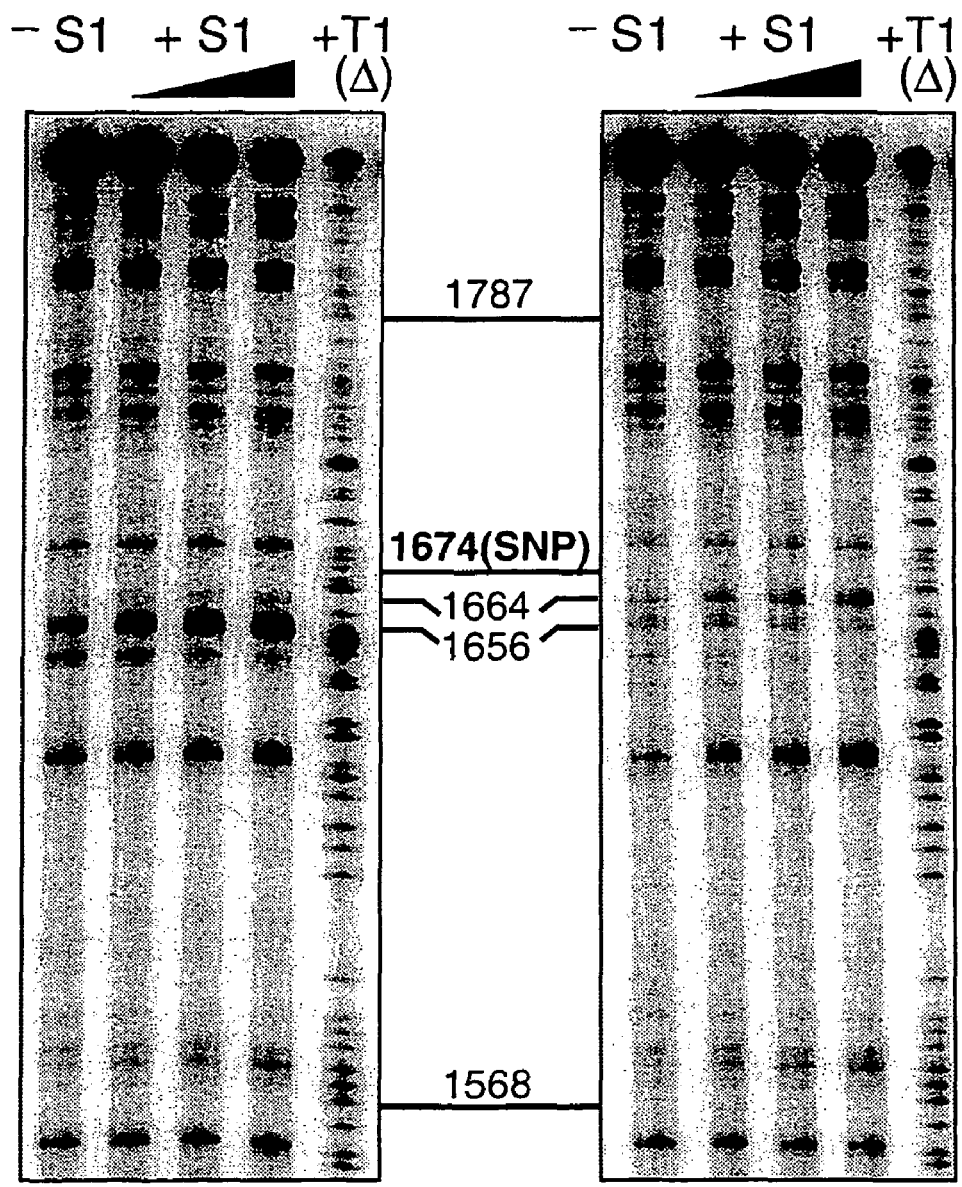
Figure 2B:
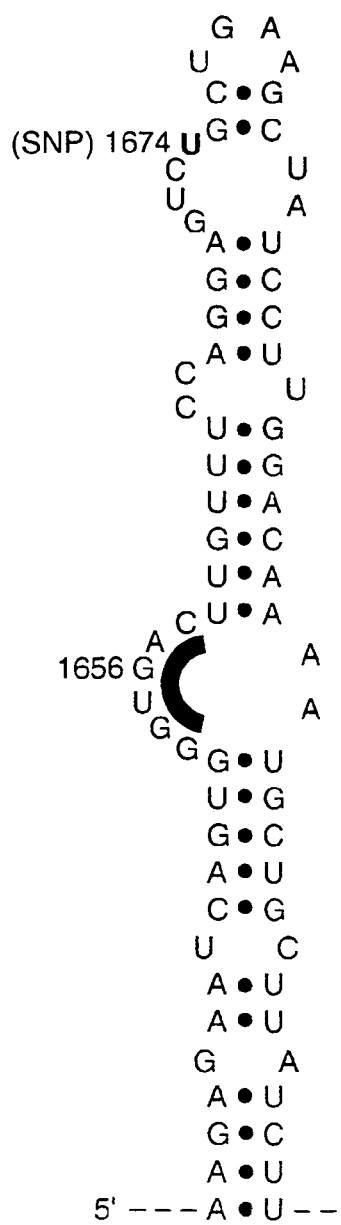
FIG. 2. Proposed secondary structural models of the polymorphic regions of the pairs of mRNA alleles. The polymorphic bases are shown boldfaced and labeled SNP. The model building was assisted by the use of computer program MFOLD (M. Zuker, Washington University, St. Louis, Mo.). Only modeled regions supported by structural mapping data are shown. a, Proposed allelic structures of the polymorphic region of AARS mRNA (SEQ ID NOs:2 and 3). The models are consistent with the data on structural mapping by nuclease S1 and RNase T1. The black bar highlights the single-stranded region around nucleotide 999 of the U-allele. b, Proposed allelic structures of the polymorphic region of RPA70 mRNA (SEQ ID NOs:4 and 5). The models are consistent with the data on structural mapping by nuclease S1. The black bar highlights the single-stranded region around nucleotide 1656 of the U-allele.
Figure 2B:
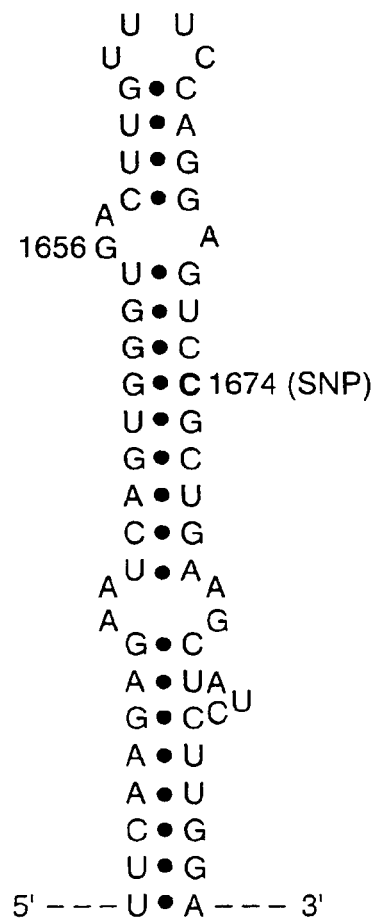

Pronounced allelic structural differences caused by a single nucleotide, variation in the mRNA sequence were also detected in a 544-nucleotide fragment of RPA70 mRNA (FIG. 1*b*). The fragment, consisting of nucleotides 1378-1921, was centered about the 1674U/C polymorphism. Intense S1 cleavages were detected in the U-allele around nucleotide 1656, indicating the presence of a single-stranded region approximately 18 nucleotides upstream of the SNP. In contrast, no cleavage above background intensity was detected at the same site of the C-allele. Differential S1 cleavage between the two alleles was also observed at nucleotide 1664 where the U-allele was more weakly cleaved than the C-allele. These data thus defined a differential-structure motif between the two allelic forms of RPA70 mRNA, with a maximum allelic difference in S1 accessibility in the region of nucleotide 1656. In addition, the structural mapping data on both the RPA70 and the AARS mRNAs revealed that the polymorphic sites were relatively inaccessible by single-strand-specific nuclease S1. Proposed secondary structural models of the polymorphic regions of the pairs of mRNA alleles are shown in FIG. 2.

Since the SNP-dependent allelic structural differences described above were identified using mRNA fragments in a purified system, it is critical to examine whether our findings of allele-specific structural features exist in the context of full-length mRNA in a protein-rich environment mimicking the physiological conditions in cells. To address this issue, we used a structure-based mRNA targeting strategy to monitor allelic structural accessibility of RPA70 mRNA in two different assay systems: a purified system containing mRNA fragments and a cell-mimicking system containing endogenous human RPA70 mRNA. We designed a series of phosphorothioate oligodeoxyribonucleotides (PS-oligos) complementary to the 1656 region of RPA70 mRNA that contains the maximum allelic difference in structural accessibility as identified by S1 mapping. The target site at the region of 1656 was chosen to span 20 or 15 nucleotides that do not include the 1674U/C polymorphism. Thus, the target site was identical in nucleotide sequence between the U- and C-alleles, and was predicted based on S1 mapping results to be accessible for PS-oligo binding in the U-allele; and inaccessible in the C-allele. Exogenous or endogenous RNase H, which cleaves RNA in RNA•DNA hybrids (26), was used to monitor the targeting efficiencies of PS-oligos for the two alleles of RPA70 mRNA.

Example 6

Figures 3A, 3B, 3C:
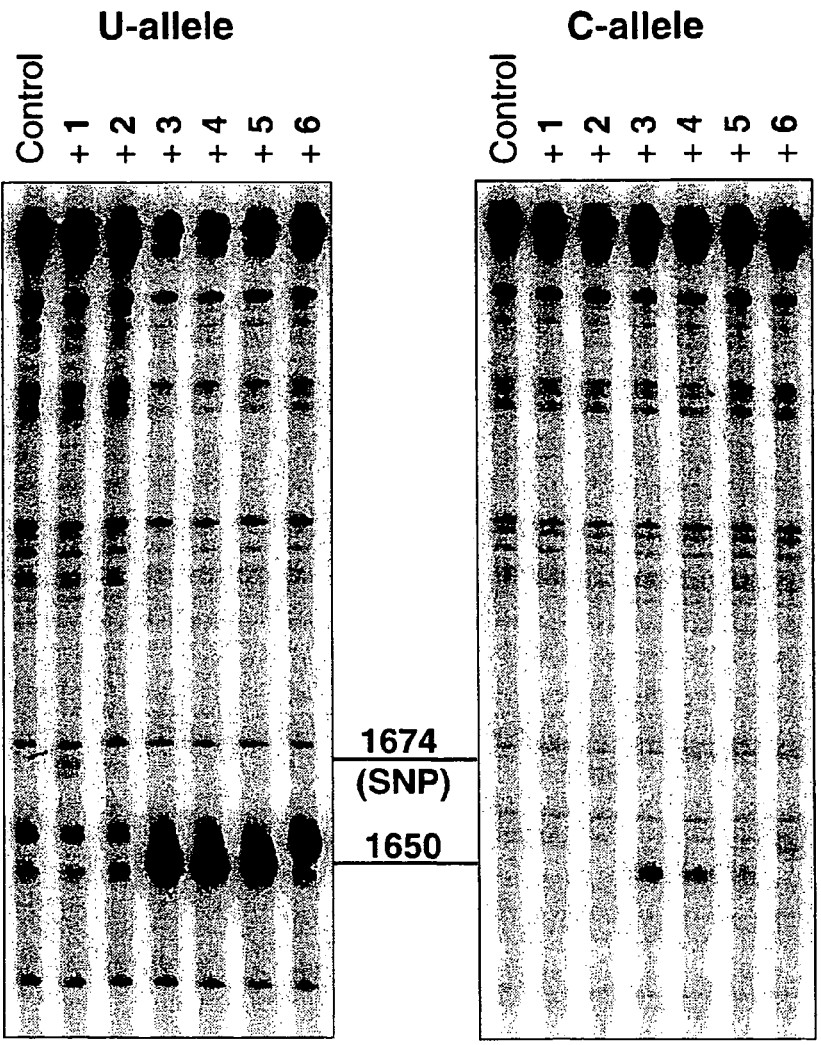
FIG. 3. *E. coli* RNase H digestion of both alleles of the 544-mer fragment of the RPA70-1674U/C mRNA. a, Nucleotide sequence of the PS-oligos used in the assay. Oligos 1 and 2 (SEQ ID NOs:6 and 7, respectively) target the polymorphic site; the bases opposing the polymorphism in the mRNA are shown in boldface. Oligos 3 and 6 (SEQ ID NOs:8 and 11, respectively) target the site of different allelic structures around nucleotide 1656. The terminal residues of oligos 1, 2, 3, and 6 (SEQ ID NOs:6, 7, 8, and 11, respectively) are labeled according to the positions of the complementary nucleotides in RPA70 mRNA. Oligos 4 and 5 (SEQ ID NOs:9 and 10, respectively) share the same target hybridization sequence as 3 (SEQ ID NO:8), but with additional nucleotides (shown underlined) added to facilitate folding into hairpin structures for intended enhancement in allele discrimination. b, *E. coli* RNase H digestion patterns of the 5'-$^{32}$P-labeled U- and C-alleles hybridized to the oligos in a. Cleavage sites were confirmed by running on the same gel RNase T1 digestion ladders for the two alleles (not shown): they are centered at position 1674 for oligos 1 and 2 (SEQ ID NOs:6 and 7), 1650 for oligos 3-5 (SEQ ID NOs:8-10), and 1654 for oligo 6 (SEQ ID NO:11). c, Comparison of percent cleavages of the U- and C-alleles calculated from b. Oligo-dependent-cleavage bands were integrated as a percentage of total RNA in each lane with the overlapping background-cleavage bands subtracted. Variations in sample loading to each lane were internally corrected by measuring percent cleavage instead of absolute band intensity.

Allele-specific Cleavage of RPA70 mRNA in a Purified System. We first used an in vitro assay with *E. coli* RNase H and the in vitro transcribed 544-mer RPA70 mRNA fragments to examine the efficiency and allele specificity of structure-based targeting as compared to directly targeting the 1674U/C polymorphism. FIG. 3a shows nucleotide sequences of the PS-oligos designed to target the RPA70 polymorphism (1, U-allele specific; 2, C-allele specific) or the site of maximum differential structural accessibility in the 1656 region (3-6). SNP-targeting oligos 1 and 2 were previously optimized for allele discrimination in a cell transfection assay (J. P. Basilion, unpublished results). Each of the SNP-targeting oligos is perfectly matched only with one of the two alleles; it is singly mismatched with the other allele. Single base mismatches formed between the SNP-targeting oligos and their respective non-targeting alleles contribute to the allele discrimination observed previously. Structure-targeting oligos 3 and 6 match perfectly with both alleles, and were designed to hybridize maximally with the single-stranded 1656 region of the U-allele, while avoiding the 1664 region which is slightly accessible in both alleles (FIG. 1b). Four and six additional nucleotides were added to the 5'-end of oligo 3 to produce oligos 4 and 5, respectively, to facilitate folding into hairpin structures for enhanced allele discrimination (27).

Results of oligo-directed, site-specific cleavage of the 544-mer U- and C-alleles by *E. coli* RNase H are shown in FIG. 3b-c. As predicted, the U-allele that was more sensitive to S1 cleavage than the C-allele in the 1656 region was over 10-fold more efficiently cleaved by *E. coli* RNase H in the presence of structure-targeting PS-oligos 3-6. Also as expected, the cleavage efficiencies with PS-oligos 1 and 2 that target the SNP at position 1674 were greater for their respective matched alleles than for the mismatched alleles. Moreover, the oligos targeting the polymorphic site were much less effective in inducing target cleavage than the oligos targeting the single-stranded-structure site of the U-allele: an approximately 14- to 25-fold reduction in cleavage efficiency was observed. This is consistent with the polymorphic site being less accessible than the single-stranded 1656 region in the U-allele, as identified by S1 mapping.

Oligos 4 and 5 with predicted hairpin structures exhibited a 23% or 36% reduction, respectively, in the cleavage of both alleles as compared to their parent oligo 3. Therefore, no enhancement in allele discrimination was obtained with oligos 4 and 5 under the experimental conditions.

Example 7

Allele-specific Cleavage of Endogenous RPA70 mRNA in Human Cell Extracts. We next performed oligo-directed cleavage of the full-length, endogenous RPA70 mRNA in whole cell extracts prepared from two genotyped human cell lines, HeLa (1674U) and Calu-1 (1674C). Cell lysis conditions were chosen to allow the disruption of both the plasma and the nuclear membranes in the absence of denaturants deleterious to the integrity of cellular proteins and nucleic acids. In order to evaluate variations between the two different cell types, we introduced a non-allele-specific, 20-mer PS-oligo 7 to the assay. Oligo 7 is complementary to the 2230-2249 sequence region of the 3'-UTR of human RPA70 mRNA; it was previously shown to target the 1674U- and 1674C-alleles with equally high efficiency in a cell transfection assay (J. P. Basilion, unpublished results).

FIG. 4 compares the extent of site-specific cleavage of the 1674U- and 1674C-alleles of the endogenous human RPA70 mRNA in the presence of 100, 300 and 600 nM of either U- or C-allele-specific oligos 1, 2, 3 and 6, or oligo 7 that targets both alleles. Both the full-length and one or two cleavage products were detected by Northern blot hybridization using [$\alpha$-$^{32}$P]dCTP-labeled cDNA probes complementary to nucleotides 1519-2080 of RPA70 mRNA. Since no *E. coli* RNase H was added to the reaction mixture, the site-specific cleavage of the mRNA is attributable to the presence of endogenous human RNase H in the cell extracts. Quantitative analysis of the extent of mRNA cleavage was done by integrating the full-length mRNA signal instead of the cleavage products. The latter did not hybridize with probes to the same extent because of probe design and were also likely more susceptible to inhomogeneous degradation by RNases in the cell extracts. The variation in sample loading was accounted for by probing a non-targeted message, glyceraldehyde 3-phosphate dehydrogenase (GAPDH), in the same Northern blots.

Figure 4A:
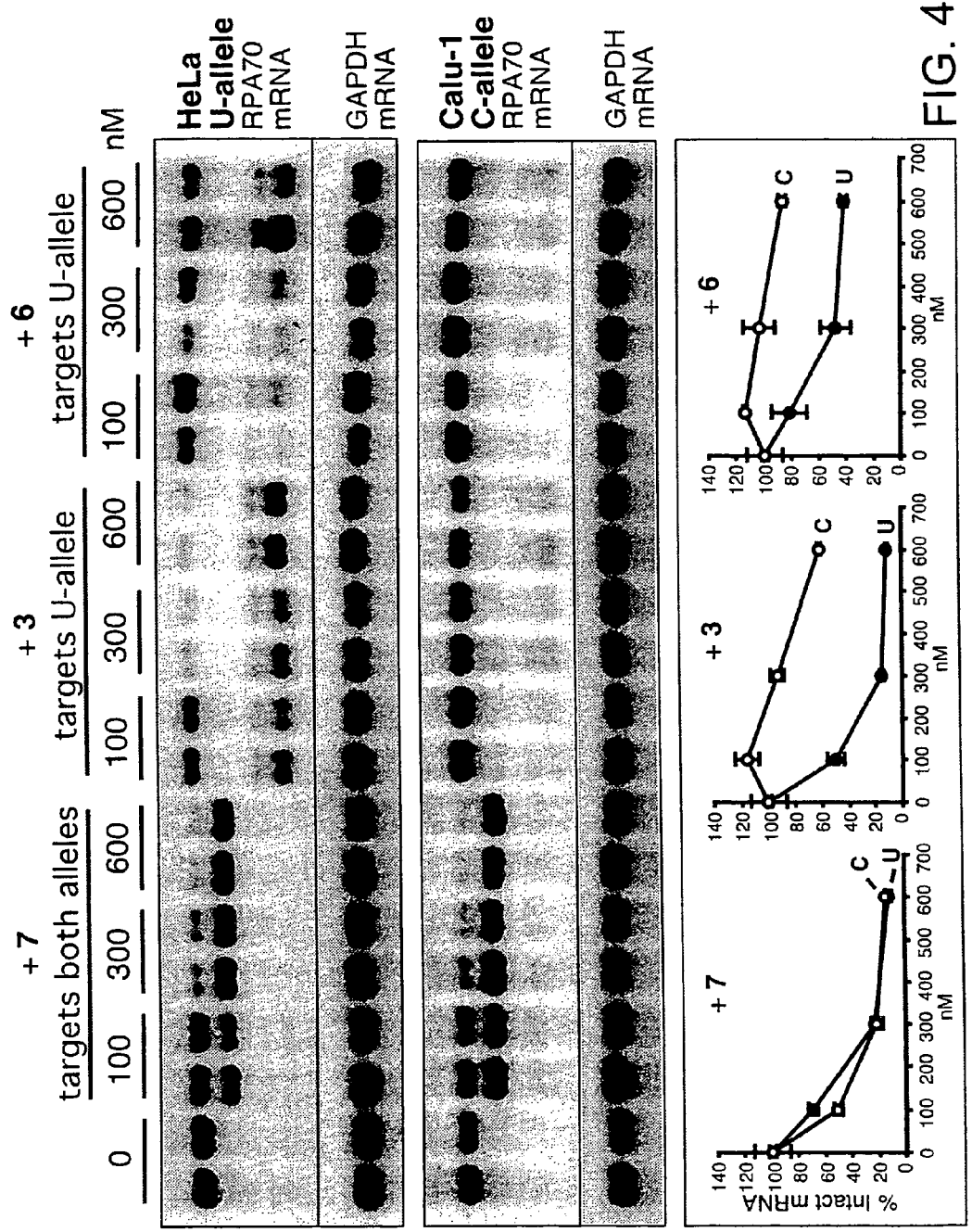
FIG. 4. Northern blot analysis of oligonucleotide-directed cleavage of endogenous RPA70 mRNA in human cell extracts. The extracts were prepared from HeLa and Calu-1 cells that express only the 1674U- or the 1674 C-allele of the RPA70 mRNA, respectively. In addition to PS-oligos 1, 2, 3, and 6 as described in FIG. 3, oligo 7 (5' TGGTCTGCAGTTAGGGTCAG 3'; SEQ ID NO:1) was used in the assay as a non-allele-specific control oligo that targets nucleotides 2230-2249 of the 3'-UTR of RPA70 mRNA. a, Targeting the 1674U/C polymorphic site by oligos 1 and 2. b, Targeting the site of different allelic structures around nucleotide 1656 by oligos 3 and 6. Reactions were done in duplicates. The averaged data points of the duplicates are plotted with standard deviations as error bars, and are shown below the corresponding Northern blots. Intact RPA70 mRNA levels were normalized to GAPDH levels and expressed as a percentage of no-oligo control for each experiment.
Figure 4B:
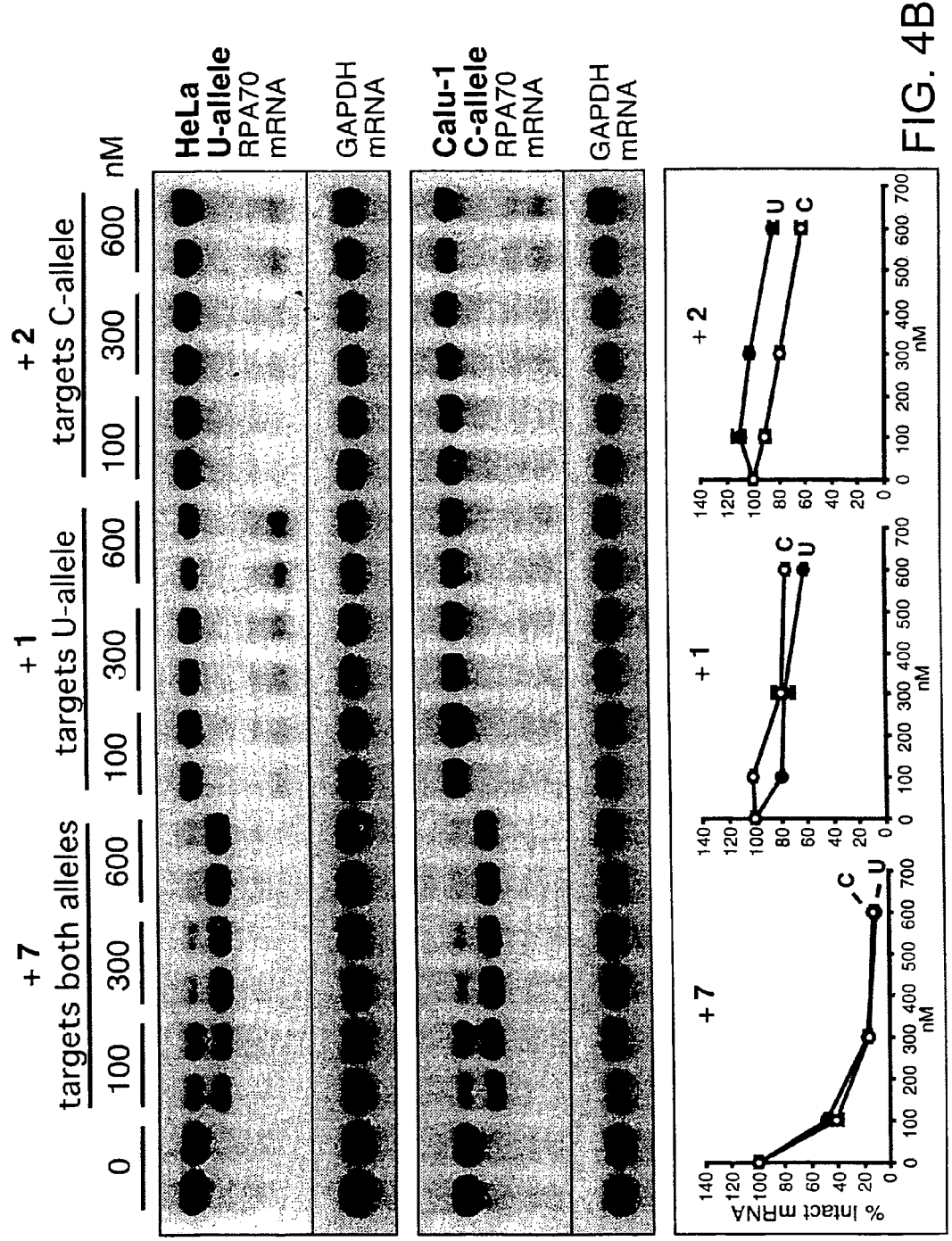
Figure 5A:
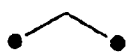
FIGS. 5A and 5B show the general structures of certain species which can be used as linkers in the present invention.
Figure 5A:
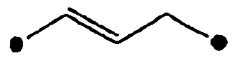
Figure 5A:
Figure 5A:
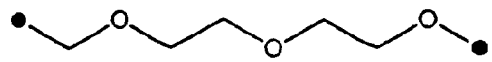
Figure 5A:
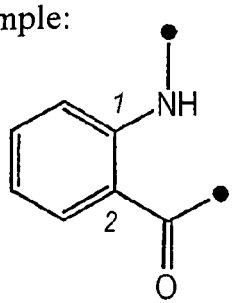
Figure 5A:
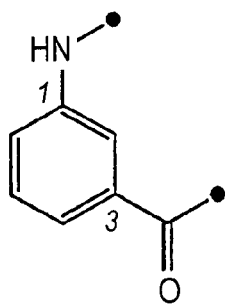
Figure 5A:
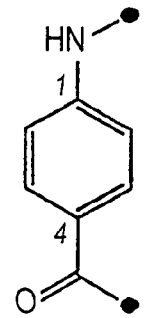
Figure 5A:
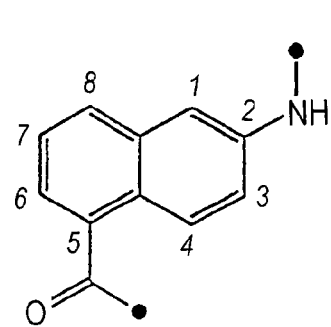
Figure 5A:
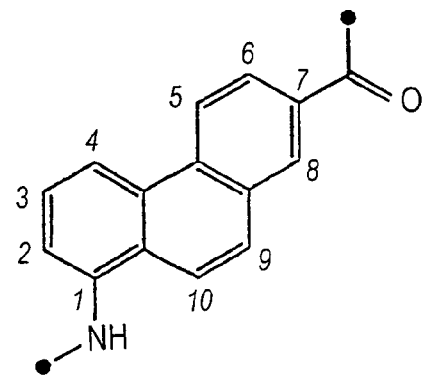
Figure 5B:
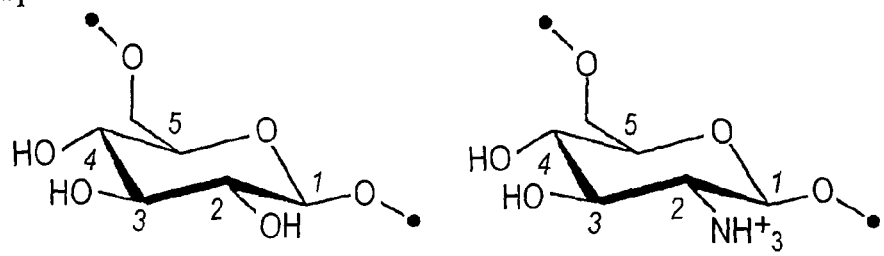
Figure 5B:
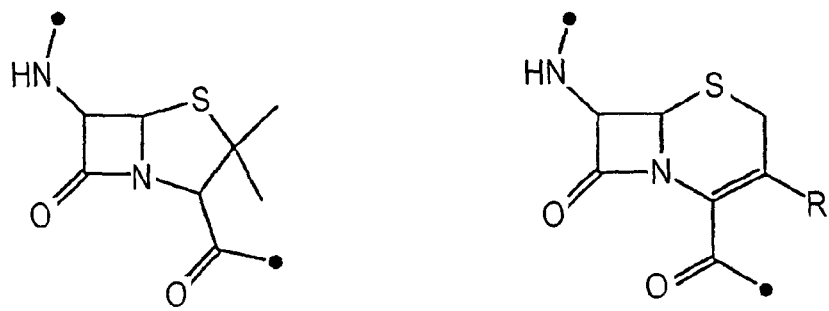

The two cell types responded similarly to the addition of control oligo 7 over a concentration range of 100 to 600 nM (FIG. 4). In contrast, oligos 1, 2, 3 and 6 displayed various degrees of targeting efficiency in an allele-specific pattern similar qualitatively to the results obtained in the purified system. In the presence of 300 nM of 20-mer 1 or 18-mer 2 targeting the 1674U/C polymorphic site, the majority of the matched allele remained uncleaved, and the matched allele was equally or slightly more cleaved than the singly mismatched allele (FIG. 4a). These results can be explained by the inaccessibility of the 1674U/C polymorphic site as identified by in vitro structural mapping, and by the predicted small difference in $\Delta G°$ of duplex formation (ca. 1-2 kcal mol$^{-1}$) (28, 29) between the matched and singly mismatched heteroduplexes. On the other hand, in the presence of 300 nM 20-mer 3 that targets the single-stranded structural motif of the U-allele, only 15% of the U-allele remained uncleaved, while more than 90% of the non-target C-allele was intact (FIG. 4b). Such high efficiency and specificity of U-allele targeting by 3 is consistent with an accessible single-stranded structure in the 1656 region of the U-allele and an inaccessible structure in the same region of the C-allele (see FIGS. 1b, 2b). Based on the data in FIG. 4, we conclude that under the experimental conditions, the allele discrimination obtained by targeting the different allelic structures of RPA70 mRNA with 20-mer 3 is two- to sixfold greater than that obtained by directly targeting the polymorphism with 20-mer 1 when the percentage of intact mRNA is evaluated. The 15-mer oligo 6 also showed better allele discrimination than the SNP-targeting oligos 1 and 2 at all three oligo concentrations, albeit less prominent than that of 20-mer 3.

It is important to note that the minor allele discrimination observed with the SNP-targeting oligos stemmed from the difference in $\Delta G°$ of duplex formation between the matched and singly mismatched heteroduplexes, as well as the differential RNase H activities associated with the matched and singly mismatched duplexes. In contrast, complete complementarity of the structure-targeting oligos with their target site sequences is expected for both the target and non-target alleles, because these target sites do not contain the polymorphism. Thus, the greater allele discrimination by structure-targeting oligos reflects a significant difference in the target site accessibility between the two alleles. This accessibility difference could be caused by either different structural folds of the two alleles of endogenous RPA70 mRNA, or different contacts with cellular components, or both effects. The positive correlation we have observed between the results in the purified system and those in cell extracts strongly support the argument that the pronounced allele discrimination obtained with the structure-targeting oligos is caused mainly by structural differences between the two endogenous RPA70 mRNA alleles.

1. Cooper, D. N., Krawczak, M. & Antonarakis, S. E. (1995) in *The Metabolic and Molecular Bases of Inherited Disease Vol I*, eds. Scriver, C. R., Beaudet, A. L., Sly, W. S. & Valle, D. (McGraw Hill, New York), pp. 259-291.
2. Nickerson, D. A., Taylor, S. L., Weiss, K. M., Clark, A. G., Hutchinson, R. G., Stengård, J., Salomaa, V., Vartiainen, E., Boerwinkle, E. & Sing, C. F. (1998) *Nature Genet.* 19, 233-240.
3. Wang, D. G. et al. (1998) *Science* 280, 1077-1082.
4. Lander, E. S. (1996) *Science* 274, 536-539.
5. Collins, F. S., Guyer, M. S. & Chakravarti, A. (1997) *Science* 278, 1580-1581.
6. Weber, W. W. (1997) *Pharmacogenetics* (Oxford University Press, New York).
7. Kleyn, P. W. & Vesell, E. S. (1998) *Science* 281, 1820-1821.
8. Coleman, T. P. & Roesser, J. R. (1998) *Biochemistry* 37, 15941-15950.
9. Côté, J. & Chabot, B. (1997) RNA 3, 1248-1261.
10. van Gelder, C. W. G., Gunderson, S. I., Jansen, E. J. R., Boelens, W. C. Polycarpou-Schwarz, M., Mattaj, I. W. & van Venrooij, W. J. (1993) *EMBO J.* 12, 5191-5200.
11. Allain, F. H.-T., Gubser, C. C., Howe, P. W. A., Nagai, K., Neuhaus, D. & Varani, G. (1996) *Nature* 380, 646-650.
12. Vasserot, A. P., Schaufele, F. J. & Bimstiel, M. L. (1989) *Proc. Natl. Acad. Sci. USA* 86, 4345-4349.
13. Pelletier, J. & Sonenberg, N. (1987) *Biochem. Cell Biol.* 65, 576-581.
14. Wang, C., Samow, P. & Siddiqui, A. (1994) *J. Virol.* 68, 7301-7307.
15. ten Dam, E. B., Pleij, C. W. A. & Bosch, L. (1990) *Virus Genes* 4, 121-136.
16. Shen, L. X. & Tinoco, I., Jr. (1995) *J. Mol. Biol.* 247, 963-978.
17. Hentze, M. W., Caughman, S. W., Rouault, T. A., Barriocanal, J. G., Dancis, A., Harford, J. B. & Klausner, R. D. (1987) *Science* 238, 1570-1573.
18. Casey, J. L., Koeller, D. M., Ramin, V. C., Klausner, R. D. & Harford, J. B. (1989) *EMBO J.* 8, 3693-3699.
19. Addess, K. J., Basilion, J. P., Klausner, R. D., Rouault, T. A. & Pardi, A. (1997) *J. Mol. Biol.* 274, 72-83.
20. Shaw, J.-P., Kent, K., Bird, J., Fishback, J. & Froehler, B. (1991) *Nucleic Acids Res.* 19, 747-750.
21. Dignam, J. D., Lebovitz, R. M. & Roeder, R. G. (1983) *Nucleic Acids Res.* 11, 1475-1489.
22. Peppel, K. & Baglioni, C. (1990) *BioTechniques* 9, 711-713.
23. Brown, T. & Mackey, K. (1997) in *Current Protocols in Molecular Biology Vol. I*, eds. Ausubel, F. M. et al. (John Wiley & Sons), pp. 4.9.1-4.9.16.
24. Wurst, R. M., Voumakis, J. N. & Maxam, A. M. (1978) *Biochemistry* 17, 4493-4499.
25. Ehresmann, C., Baudin, F., Mougel, M., Romby, P., Ebel, J.-P. & Ehresmann, B. (1987) *Nucleic Acids Res.* 15, 9109-9128.
26. Hostomsky, Z., Hostomska, Z. & Matthews, D. A. (1993) in *Nucleases*, eds. Linn, S. M., Lloyd, R. S. & Roberts, R. J. (Cold Spring Harbor Laboratory, New York), pp. 341-376.
27. Tyagi, S., Bratu, D. P. & Kramer, F. R. (1998) *Nature Biotech.* 16, 49-53.
28. Aboul-ela, F., Koh, D. & Tinoco, I., Jr. (1985) *Nucleic Acids Res.* 13, 4811-4824.
29. Freier, S. M., Kierzek, R., Jaeger, J. A., Sugimoto, N., Caruthers, M. H., Neilson, T. & Turner, D. H. (1986) *Proc. Natl. Acad. Sci. USA* 83, 93.73-9377.
30. Werstuck, G. & Green, M. R. (1998) *Science* 282, 296-298.
31. Mei, H.-Y., Cui, M., Heldsinger, A., Lemrow, S. M., Loo, J. A., Sannes-Lowery, K. A., Sharmeen, L. & Czarnik, A. W. (1998) *Biochemistry* 37, 14204-14212.
32. Hamy, F., Felder, E. R., Heizmann, G., Lazdins, Aboul-ela, F., Varani, G., Karn, J. & Klimkait, T. (1997) *Proc. Natl. Acad. Sci. USA* 94, 3548-3553.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily, appreciate that the present invention is well adapted to carry out the objects and obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other compounds, and/or methods of administration are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example; in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in thy art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What is claimed is:

1. A method for inhibiting protein expression from a target mRNA, the method comprising
contacting cells normally expressing the protein from the target mRNA, wherein the target mRNA has been identified as comprising a polymorphism leading to an altered secondary structure from the allelic form of the mRNA, with a small molecule inhibitor, the inhibitor comprising a first moiety which binds to a cellular protein that is present in cellular compartment(s) in which the target mRNA is present; a second moiety which binds to the altered secondary structure of the target mRNA, wherein the second moiety is an oligonucleotide; and a linker connecting the first moiety and the second moiety, wherein the small molecule inhibitor inhibits protein expression from the target RNA by binding to both the cellular protein and to the target mRNA to form a complex.

2. The method of claim 1, wherein said cellular protein is a human protein.

3. The method of claim 1, wherein said target mRNA is a human mRNA.

4. The method of claim 1, wherein said first moiety is a natural ligand of said cellular protein or an analog thereof.

5. The method of claim 1, wherein said cellular protein is a protein with known RNA binding activity.

6. The method of claim 1, wherein said cellular protein is a RNase.

7. The method of claim 1, wherein said cellular protein is a RNase selected from the class consisting of RNaseH type 1, RNaseH type 2, and RNaseL.

8. The method of claim 1, wherein said cellular protein is a RNA helicase.

9. The method of claim 1, wherein said cellular protein is a DNA binding protein.

10. The method of claim 1, wherein the molecular weight of said small molecule does not exceed 4000 Daltons.

11. The method of claim 1, wherein the target mRNA is a pre-mRNA.

12. The method of claim 1 wherein the first moiety is selected from FAD, folate, cyclosporine, FK506, rapamycin and coumermycin.

* * * * *

UNITED STATES PATENT AND TRADEMARK OFFICE
CERTIFICATE OF CORRECTION

| | |
|---|---|
| PATENT NO. | : 8,389,484 B2 |
| APPLICATION NO. | : 10/999171 |
| DATED | : March 5, 2013 |
| INVENTOR(S) | : Ling X. Shen |

Page 1 of 1

It is certified that error appears in the above-identified patent and that said Letters Patent is hereby corrected as shown below:

On the Title Page, Col. 2, item (56) (Other Publications), line 8, delete "Strategens" and insert -- Strategems --

On the Title Page, Col. 2, item (56) (Other Publications), line 11, delete "Single0nucleotide" and insert -- Single-nucleotide --

Signed and Sealed this
Eleventh Day of June, 2013

Teresa Stanek Rea
*Acting Director of the United States Patent and Trademark Office*

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tggtctgcag ttagggtcag                                                   20

<210> SEQ ID NO 2
<211> LENGTH: 27
<212> TYPE: RNA
<213> ORGANISM: Homo sapiens

<400> SEQUENCE: 2
gggugcuggc ugaccaugcu cggacca                                           27

<210> SEQ ID NO 3
<211> LENGTH: 25
<212> TYPE: RNA
<213> ORGANISM: Homo sapiens

<400> SEQUENCE: 3
ccgggugcug gcugaccacg cucgg                                             25

<210> SEQ ID NO 4
<211> LENGTH: 71
<212> TYPE: RNA
<213> ORGANISM: Homo sapiens

<400> SEQUENCE: 4
aagagaauca gugggugacu uguuccagg agucugcuga agcuauccuu ggacaaaaug        60
cugcuuaucu u                                                            71

<210> SEQ ID NO 5
<211> LENGTH: 56
<212> TYPE: RNA
<213> ORGANISM: Homo sapiens

<400> SEQUENCE: 5
uucaagagaa ucagugggug acuuguuucc aggaguccgc ugaagcuauc cuugga           56

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
tagcttcagc agactcctgg                                                   20
```

```
<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 7
gcttcagcgg actcctgg                                                 18

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
caagtcaccc actgattctc                                               20

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
gaatcaagtc acccactgat tctc                                          24

<210> SEQ ID NO 10
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 10
gagaatcaag tcacccactg attctc                                        26

<210> SEQ ID NO 11
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 11
caagtcaccc actga                                                    15
```